US006872406B2

(12) United States Patent
Qi

(10) Patent No.: US 6,872,406 B2
(45) Date of Patent: Mar. 29, 2005

(54) FUSOGENIC PROPERTIES OF SAPOSIN C AND RELATED PROTEINS AND POLYPEPTIDES FOR APPLICATION TO TRANSMEMBRANE DRUG DELIVERY SYSTEMS

(75) Inventor: Xiaoyang Qi, Cincinnati, OH (US)

(73) Assignee: Children's Hospital Research Foundation, Cincinnati, OH (US)

( * ) Notice: Subject to any disclaimer, the term of this patent is extended or adjusted under 35 U.S.C. 154(b) by 27 days.

(21) Appl. No.: 09/780,438

(22) Filed: Feb. 9, 2001

(65) Prior Publication Data

US 2003/0095999 A1 May 22, 2003

Related U.S. Application Data

(60) Provisional application No. 60/181,754, filed on Feb. 11, 2000.

(51) Int. Cl.[7] .............................................. A61K 9/127

(52) U.S. Cl. ..................................................... 424/450

(58) Field of Search ............................... 424/450, 94.3; 530/300, 350; 514/1, 2

(56) References Cited

U.S. PATENT DOCUMENTS

| | | | | |
|---|---|---|---|---|
| 5,766,626 A | | 6/1998 | Gross | |
| 5,911,983 A | | 6/1999 | Barranger et al. | |
| 6,099,857 A | | 8/2000 | Gross | |
| 2002/0127219 A1 | * | 9/2002 | Okkels et al. | 424/94.61 |

FOREIGN PATENT DOCUMENTS

| | | | | |
|---|---|---|---|---|
| WO | WO 9503821 A1 | * | 2/1995 | A61K/38/18 |

OTHER PUBLICATIONS

Shechter, E., Gulik–Krzywicki, T., Azerad, R., and Gros, C. (1971) *Biochim. Biophys. Acta* 241, 431–442.

Berent, S.L., and Radin, N.S. (1981) *Biochim. Biophys. Acta* 664, 572–582.

Fujibayashi, S., Kao, F.T., Jones, C., Morse, H., Law, M., and Wenger, D.A. (1985) *Am.J. Hum. Genet.* 37, 741–748.

Fujibayashi, S., and Wenger, D.A. (1986) *J.Biol. Chem. 261*, 15339–15343.

Fujibayashi, S., and Wenger, D.A. (1986) *Biochim. Biophys. Acta* 875, 554–562.

Conzelmann, E., and Sandhoff, K. (1987) *Methods Enzymol.* 138, 792–815.

O'Brien, J.S., Kretz, K.A., Dewji, N., Wenger, D.A., Esch, F., and Fluharty, A.L. (1988) *Science* 241, 1098–1101.

Sano, A., and Radin, N.S. (1988) *Biochem. Biophys. Res. Commun.* 154, 1197–1203.

Morimoto, S., Martin, B.M., Kishimoto, Y., and O'Brien, J.S. (1988) *Biochem. Biophys. Res. Commun.* 156, 403–410.

Rorman, E.G., and Grabowski, G.A. (1989) *Genomics* 5, 486–492.

Nakano, T., Sandhoff, K., Stumper, J., Christomanou, H., and Suzuki, K. (1989) *J. Biochem.* (*Tokyo*) 105, 152–154.

Reiner, O., Dagan, O., and Horowitz, M. (1989) *J.Mol. Neurosci.* 1, 225–233.

Morimoto, S., Martin, B.M., Yamamoto, Y., Kretz, K.A., O'Brien, J.S., and Kishimoto, Y., (1989) *Proc. Natl. Acad. Sci. U.S.A.* 86, 3389–3393.

Wenger, D.A., DeGala, G., Williams, C., Taylor, H.A., Stevenson, R.E., Pruitt, J.R., Miller, J., Garen, P.D., and Balentine, J.D. (1989) *Am. J. Med. Genet.* 33, 255–265.

Grabowski, G.A., Gatt, S., and Horowitz, M. (1990) *Crit. Rev. Biochem. Mol. Biol.* 25, 385–414.

Greenberg, P., Merrill, A.H., Liotta, D.C., and Grabowski, G. A. (1990) *Biochim. Biophys. Acta* 1039, 12–20.

Morimoto, S., Yamamoto, Y., O'Brien, J.S., and Kishimoto, Y. (1990) *Proc. Natl. Acad. Sci. U.S.A.* 87, 3493–3497.

Schnable, D., Schroder, M., and Sandhoff, K. (1991) *FEBS Lett.* 284, 57–59.

Furst, W., and Sandhoff, K., (1992) *Biochim. Biophys. Acta* 1126, 1–16.

Kishimoto, Y., Hiraiwa, M., and O'Brien, J.S. (1992) *J. Lipid. Res.* 33, 1255–1267.

Vandenbussche, G., Clercx, A., Clercx, M., Curstedt, T., Johansson, J., Jornvall, H., and Ruysschaert, J.M. (1992) *Biochemistry* 31, 9169–9176.

Schnabel, D., Schroder, M., Furst, W., Klien, A., Hurwitz, R., Zenk, T., Weber, J., Harzer, K., Paton, B.C., Poulos, A., Suzuki, K., and Sandhoff, K. (1992) *J. Biol. Chem.* 267, 3312–3315.

Hiraiwa, M., Soeda, S., Martin, B.M., Fluharty, A. L., Hirabayashi, Y., O'Brien, J.S., and Kishimoto, Y. (1993) *Arch. Biochem. Biophy.* 303, 326–331.

Rafi. M.A., de Gala, G., Zhang, X.L., and Wenger, D.A. (1993) *Somat. Cell Mol. Genet.* 19, 1–7.

Qi, X., Leonova, T., and Grabowski, G.A. (1994) *J. Biol.Chem.* 269, 16746–16753.

Klein, A., Henseler, M., Klein, C., Suzuki, K., Harzer, K., and Sandhoff, K. (1994) *Biochem. Biophys. Res. Commun.* 200, 1440–1448.

(Continued)

*Primary Examiner*—Karen Cochrane Carlson
*Assistant Examiner*—Sheridan K Snedden
(74) *Attorney, Agent, or Firm*—Frost Brown Todd LLC

(57) ABSTRACT

The present invention comprises a method for delivering pharmaceutical agents within and/or through the dermal and mucosal membranes, utilizing a fusogenic protein. The fusogenic protein is associated with a phospholipid membrane, such as a liposome. The liposome contains the pharmaceutical agent. Preferred fusogenic proteins include saposin C and other proteins, polypeptides and peptide analogs derived from saposin C. The active agent contained within the liposome may comprise large biomolecules and/or small organic molecules. This technology can be used for both cosmetic and medicinal applications in which the objective is delivery of the active agent within and/or beneath the biological membrane.

44 Claims, 5 Drawing Sheets

OTHER PUBLICATIONS

Vaccaro, A.M. et al. (1994) *FEBS Letters* 349, 181–186.
Vaccaro, A.M., Salvioli, R., Barca, A., Tatti, M., Ciaffoni, F., Maras, B., Siciliano, R., Zappacosta, F., Amoresano, A., and Pucci, P. (1995) *J. Biol. Chem.* 270, 9953–9960.
Munford, R.S., Sheppard, P.O., and O'Hara, P.J. (1995) *J. Lipid. Res.* 36, 1653–1663.
Whitsett, J.A., Nogee, L.M., Weaver, T.E., and Horowitz, A.D. (1995) *Physiol. Rev.* 75, 749–757.
Andersson, M., Gunne, H., Agerberth, B., Boman, A., Bergman, T., Sillard, R., Jornvall, H., Mutt, V., Olsson, B., Wigzell, H. (1995) *EMBO J.* 14, 1615–1625.
Vaccaro, A.M., Ciaffoni, F., Tatti, M., Salvioli, R., Barca, A., Tognozzi, D., and Scerch, C. (1995) *J. Biol. Chem.* 270, 30576–30580.
Qi, X., Qin, W., Sun, Y., Kondoh, K., and Grabowski, G.A. (1996) *J. Biol. Chem.* 271, 6874–6880.
Liepinsh, E., Andersson, M., Ruysschaert, J.M., and Otting, G., (1997) *Nat. Struct. Biol.* 4, 793–795.
Harzer, K., Paton, B.C., Christomanou, H., Chatelut, M., Levade, T., Hiraiwa, M. and O'Brien, J.S. (1997) *FEBS Lett.* 417, 270–274.
Vaccaro, A.M., Tatti, M., Ciaffoni, F., Salvioli, R., Barca, A., and Scerch, C. (1997) *J.Biol. Chem.* 272, 16862–16867.
Qi, X., and Grabowski, G.A. (1998) *Biochemistry* 37, 11544–11554.
Kervinen, J., Tobin, G.J., Costa, J., Waugh, D.S., Wlodawer, A., and Zdanov, A. (1999) *EMBO J.* 18, 3947–3955.
Regis, S., Filocamo, M., Corsolini, F., Caroli, F., Keulemans, J.L., van Diggelen, O.P., and Gatti, R. (1999) *Eur. J. Hum. Genet.* 7, 125–130.
Qi, X., Kondoh, K., Krusling, D., Kelso, G.J., Leonova, T., and Grabowski, G.A. (1999) *Biochemistry* 38, 6284–6291.

* cited by examiner

Clip-on Model: Saposin C - Induced Fusion

SEQUENCE LISTING

```
<160> NUMBER OF SEQ ID NOS: 6

<210> SEQ ID NO 1
<211> LENGTH: 40
```

-continued

```
<212> TYPE: PRT
<213> ORGANISM: Homo sapiens

<400> SEQUENCE: 1

Ser Asp Val Tyr Cys Glu Val Cys Glu Phe Leu Val Lys Glu Val Thr
1               5                   10                  15

Lys Leu Ile Asp Asn Asn Lys Thr Glu Lys Glu Ile Leu Asp Ala Phe
            20                  25                  30

Asp Lys Met Cys Ser Lys Leu Pro
        35                  40


<210> SEQ ID NO 2
<211> LENGTH: 38
<212> TYPE: PRT
<213> ORGANISM: Homo sapiens

<400> SEQUENCE: 2

Val Tyr Cys Glu Val Cys Glu Phe Leu Val Lys Glu Val Thr Lys Leu
1               5                   10                  15

Ile Asp Asn Asn Lys Thr Glu Lys Glu Ile Leu Asp Ala Phe Asp Lys
            20                  25                  30

Met Cys Ser Lys Leu Pro
        35


<210> SEQ ID NO 3
<211> LENGTH: 38
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Where the amino acid located at 1 is a
      hydrophobic amino acids, including Val, Leu, Ile, Met, Pro,
      Phe, and Ala
<220> FEATURE:
<221> NAME/KEY: MISC_FEATURE
<222> LOCATION: (2)..(2)
<223> OTHER INFORMATION: Where the amino acid located at 2 is an
      uncharged polar amino acid, including Thr, Ser, Tyr, Gly, Gln,
      and Asn
<220> FEATURE:
<221> NAME/KEY: MISC_FEATURE
<222> LOCATION: (5)..(5)
<223> OTHER INFORMATION: Where the amino acid located at 5 is a
      hydrophobic amino acid, including Val, Leu, Ile, Met, Pro, Phe,
      and Ala
<220> FEATURE:
<221> NAME/KEY: MISC_FEATURE
<222> LOCATION: (8)..(10)
<223> OTHER INFORMATION: Where the amino acids located at 8-10 are
      hydrophobic amino acids, including Val, Leu, Ile, Met, Pro, Phe,
      and Ala
<220> FEATURE:
<221> NAME/KEY: MISC_FEATURE
<222> LOCATION: (13)..(13)
<223> OTHER INFORMATION: Where the amino acid located at 13 is a
      hydrophobic amino acid, including Val, Leu, Ile, Met, Pro, Phe,
      and Ala
<220> FEATURE:
<221> NAME/KEY: MISC_FEATURE
<222> LOCATION: (14)..(14)
<223> OTHER INFORMATION: Where the amino acid located at 14 is an
      uncharged polar amino acid, including Thr, Ser, Tyr, Gly, Gln,
      and Asn
<220> FEATURE:
<221> NAME/KEY: MISC_FEATURE
<222> LOCATION: (16)..(17)
<223> OTHER INFORMATION: Where the amino acids located at 16 and 17
      are hydrophobic amino acids, including Val, Leu, Ile, Met, Pro,
      Phe, and Ala
<220> FEATURE:
```

-continued

```
<221> NAME/KEY: MISC_FEATURE
<222> LOCATION: (22)..(22)
<223> OTHER INFORMATION: Where the amino acid located at 22 is an
      uncharged polar amino acid, including Thr, Ser, Tyr, Gly, Gln,
      and Asn
<220> FEATURE:
<221> NAME/KEY: MISC_FEATURE
<222> LOCATION: (26)..(27)
<223> OTHER INFORMATION: Where the amino acids located at 26 and 27
      are hydrophobic amino acids, including Val, Leu, Ile, Met, Pro,
      Phe, and Ala
<220> FEATURE:
<221> NAME/KEY: MISC_FEATURE
<222> LOCATION: (29)..(30)
<223> OTHER INFORMATION: Where the amino acids located at 29 and 30 are
      hydrophobic amino acids, including Val, Leu, Ile, Met, Pro, Phe,
      and Ala
<220> FEATURE:
<221> NAME/KEY: MISC_FEATURE
<222> LOCATION: (33)..(33)
<223> OTHER INFORMATION: Where the amino acid located at 33 is a
      hydrophobic amino acid, including Val, Leu, Ile, Met, Pro, Phe,
      and Ala
<220> FEATURE:
<221> NAME/KEY: MISC_FEATURE
<222> LOCATION: (35)..(35)
<223> OTHER INFORMATION: Where the amino acid located at 35 is an
      uncharged polar amino acid, including Thr, Ser, Tyr, Gly, Gln,
      and Asn
<220> FEATURE:
<221> NAME/KEY: MISC_FEATURE
<222> LOCATION: (37)..(38)
<223> OTHER INFORMATION: Where the amino acids located at 37 and 38 are
      hydrophobic amino acids, including Val, Leu, Ile, Met, Pro, Phe,
      and Ala

<400> SEQUENCE: 3

Xaa Xaa Cys Glu Xaa Cys Glu Xaa Xaa Xaa Lys Glu Xaa Xaa Lys Xaa
1               5                   10                  15

Xaa Asp Asn Asn Lys Xaa Glu Lys Glu Xaa Xaa Asp Xaa Xaa Asp Lys
            20                  25                  30

Xaa Cys Xaa Lys Xaa Xaa
        35


<210> SEQ ID NO 4
<211> LENGTH: 39
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: Where the amino acids located at 1 and 2 are
      hydrophobic amino acids, including Val, Leu, Ile, Met, Pro, Phe,
      and Ala
<220> FEATURE:
<221> NAME/KEY: MISC_FEATURE
<222> LOCATION: (3)..(3)
<223> OTHER INFORMATION: Where the amino acid located at 3 is an
      uncharged polar amino acid, including Thr, Ser, Tyr, Gly, Gln,
      and Asn
<220> FEATURE:
<221> NAME/KEY: MISC_FEATURE
<222> LOCATION: (6)..(6)
<223> OTHER INFORMATION: Where the amino acid located at 6 is a
      hydrophobic amino acid, including Val, Leu, Ile, Met, Pro, Phe,
      and Ala
<220> FEATURE:
<221> NAME/KEY: MISC_FEATURE
<222> LOCATION: (9)..(11)
<223> OTHER INFORMATION: Where the amino acids located at 9-11 are
      hydrophobic amino acids, including Val, Leu, Ile, Met, Pro, Phe,
      and Ala
<220> FEATURE:
<221> NAME/KEY: MISC_FEATURE
<222> LOCATION: (14)..(14)
```

-continued

```
<223> OTHER INFORMATION: Where the amino acid located at 14 is a
      hydrophobic amino acid, including Val, Leu, Ile, Met, Pro, Phe,
      and Ala
<220> FEATURE:
<221> NAME/KEY: MISC_FEATURE
<222> LOCATION: (15)..(15)
<223> OTHER INFORMATION: Where the amino acid located at 15 is an
      uncharged polar amino acid, including Thr, Ser, Tyr, Gly, Gln,
      and Asn
<220> FEATURE:
<221> NAME/KEY: MISC_FEATURE
<222> LOCATION: (17)..(18)
<223> OTHER INFORMATION: Where the amino acids located at 17 and 18
      are hydrophobic amino acids, including Val, Leu, Ile, Met, Pro,
      Phe, and Ala
<220> FEATURE:
<221> NAME/KEY: MISC_FEATURE
<222> LOCATION: (23)..(23)
<223> OTHER INFORMATION: Where the amino acid located 23 is an
      uncharged polar amino acid, including Thr, Ser, Tyr, Gly,
      Gln, and Asn
<220> FEATURE:
<221> NAME/KEY: MISC_FEATURE
<222> LOCATION: (27)..(28)
<223> OTHER INFORMATION: Where the amino acids located at 27 and 28 are
      hydrophobic amino acids, including Val, Leu, Ile, Met, Pro, Phe,
      and Ala
<220> FEATURE:
<221> NAME/KEY: MISC_FEATURE
<222> LOCATION: (30)..(31)
<223> OTHER INFORMATION: Where the amino acids located at 30 and 31 are
      hydrophobic amino acids, including Val, Leu, Ile, Met, Pro, Phe,
      and Ala
<220> FEATURE:
<221> NAME/KEY: MISC_FEATURE
<222> LOCATION: (34)..(34)
<223> OTHER INFORMATION: Where the amino acid located at 34 is a
      hydrophobic amino acid, including Val, Leu, Ile, Met, Pro, Phe,
      and Ala
<220> FEATURE:
<221> NAME/KEY: MISC_FEATURE
<222> LOCATION: (36)..(36)
<223> OTHER INFORMATION: Where the amino acid located at 36 is an
      uncharged polar amino acid, including Thr, Ser, Tyr, Gly, Gln,
      and Asn
<220> FEATURE:
<221> NAME/KEY: MISC_FEATURE
<222> LOCATION: (38)..(39)
<223> OTHER INFORMATION: Where the amino acids located at 38 and 39 are
      hydrophobic amino acids, including Val, Leu, Ile, Met, Pro, Phe,
      and Ala

<400> SEQUENCE: 4

Xaa Xaa Xaa Cys Glu Xaa Cys Glu Xaa Xaa Xaa Lys Glu Xaa Xaa Lys
1               5                   10                  15

Xaa Xaa Asp Asn Asn Lys Xaa Glu Lys Glu Xaa Xaa Asp Xaa Xaa Asp
            20                  25                  30

Lys Xaa Cys Xaa Lys Xaa Xaa
        35


<210> SEQ ID NO 5
<211> LENGTH: 38
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Where the amino acid located at 1 is a
      hydrophobic amino acid, including Val, Leu, Ile, Met, Pro,
      Phe, and Ala
<220> FEATURE:
<221> NAME/KEY: MISC_FEATURE
<222> LOCATION: (2)..(2)
```

-continued

```
<223> OTHER INFORMATION: Where the amino acid located at 2 is an
      uncharged polar amino acid, including Thr, Ser, Tyr, Gly, Gln,
      and Asn
<220> FEATURE:
<221> NAME/KEY: MISC_FEATURE
<222> LOCATION: (5)..(5)
<223> OTHER INFORMATION: Where the amino acid located at 5 is a
      hydrophobic amino acid, including Val, Leu, Ile, Met, Pro, Phe,
      and Ala
<220> FEATURE:
<221> NAME/KEY: MISC_FEATURE
<222> LOCATION: (8)..(10)
<223> OTHER INFORMATION: Where the amino acids located at 8-10 are
      hydrophobic amino acids, including Val, Leu, Ile, Met, Pro, Phe,
      and Ala
<220> FEATURE:
<221> NAME/KEY: MISC_FEATURE
<222> LOCATION: (13)..(13)
<223> OTHER INFORMATION: Where the amino acid located at 13 is a
      hydrophobic amino acid, including Val, Leu, Ile, Met, Pro, Phe,
      and Ala
<220> FEATURE:
<221> NAME/KEY: MISC_FEATURE
<222> LOCATION: (14)..(14)
<223> OTHER INFORMATION: Where the amino acid located at 14 is an
      uncharged polar amino acid, including Thr, Ser, Tyr, Gly, Gln,
      and Asn
<220> FEATURE:
<221> NAME/KEY: MISC_FEATURE
<222> LOCATION: (16)..(17)
<223> OTHER INFORMATION: Where the amino acids located at 16 and 17 are
      hydrophobic amino acids, including Val, Leu, Ile, Met, Pro, Phe,
      and Ala
<220> FEATURE:
<221> NAME/KEY: MISC_FEATURE
<222> LOCATION: (22)..(22)
<223> OTHER INFORMATION: Where the amino acid located at 22 is an
      uncharged polar amino acid, including Thr, Ser, Tyr, Gly, Gln,
      and Asn
<220> FEATURE:
<221> NAME/KEY: MISC_FEATURE
<222> LOCATION: (26)..(27)
<223> OTHER INFORMATION: Where the amino acids located at 26 and 27 are
      hydrophobic amino acids, including Val, Leu, Ile, Met, Pro, Phe,
      and Ala
<220> FEATURE:
<221> NAME/KEY: MISC_FEATURE
<222> LOCATION: (29)..(30)
<223> OTHER INFORMATION: Where the amino acids located at 29 and 30 are
      hydrophobic amino acids, including Val, Leu, Ile, Met, Pro, Phe,
      and Ala
<220> FEATURE:
<221> NAME/KEY: MISC_FEATURE
<222> LOCATION: (33)..(33)
<223> OTHER INFORMATION: Where the amino acid located at 33 is a
      hydrophobic amino acid, including Val, Leu, Ile, Met, Pro,
      Phe, and Ala
<220> FEATURE:
<221> NAME/KEY: MISC_FEATURE
<222> LOCATION: (35)..(35)
<223> OTHER INFORMATION: Where the amino acid located at 35 is an
      uncharged polar amino acid, including Thr, Ser, Tyr, Gly, Gln,
      and Asn
<220> FEATURE:
<221> NAME/KEY: MISC_FEATURE
<222> LOCATION: (37)..(38)
<223> OTHER INFORMATION: Where the amino acids located at 37 and 38 are
      hydrophobic amino acids, including Val, Leu, Ile, Met, Pro, Phe,
      and Ala

<400> SEQUENCE: 5

Xaa Xaa Cys Glu Xaa Cys Glu Xaa Xaa Xaa Lys Glu Xaa Xaa Lys Xaa
1               5                   10                  15

Xaa Asp Asn Asn Lys Xaa Glu Lys Glu Xaa Xaa Asp Xaa Xaa Asp Lys
            20                  25                  30
```

-continued

```
Xaa Cys Xaa Lys Xaa Xaa
        35


<210> SEQ ID NO 6
<211> LENGTH: 38
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Where the amino acid located at 1 is a
      hydrophobic amino acid, including Val, Leu, Ile, Met, Pro, Phe,
      and Ala
<220> FEATURE:
<221> NAME/KEY: MISC_FEATURE
<222> LOCATION: (2)..(2)
<223> OTHER INFORMATION: Where the amino acid located at 2 is an
      uncharged polar amino acid, including Thr, Ser, Tyr, Gly, Gln,
      and Asn
<220> FEATURE:
<221> NAME/KEY: MISC_FEATURE
<222> LOCATION: (5)..(5)
<223> OTHER INFORMATION: Where the amino acid located at 5 is a
      hydrophobic amino acid, including Val, Leu, Ile, Met, Pro, Phe,
      and Ala
<220> FEATURE:
<221> NAME/KEY: MISC_FEATURE
<222> LOCATION: (8)..(10)
<223> OTHER INFORMATION: Where the amino acids located at 8-10 are
      hydrophobic amino acids, including Val, Leu, Ile, Met, Pro, Phe,
      and Ala
<220> FEATURE:
<221> NAME/KEY: MISC_FEATURE
<222> LOCATION: (13)..(13)
<223> OTHER INFORMATION: Where the amino acid located at 13 is a
      hydrophobic amino acid, including Val, Leu, Ile, Met, Pro, Phe,
      and Ala
<220> FEATURE:
<221> NAME/KEY: MISC_FEATURE
<222> LOCATION: (14)..(14)
<223> OTHER INFORMATION: Where the amino acid located at 14 is an
      uncharged polar amino acid, including Thr, Ser, Tyr, Gly, Gln,
      and Asn
<220> FEATURE:
<221> NAME/KEY: MISC_FEATURE
<222> LOCATION: (16)..(17)
<223> OTHER INFORMATION: Where the amino acids located at 16 and 17
      are hydrophobic amino acids, including Val, Leu, Ile, Met, Pro,
      Phe, and Ala
<220> FEATURE:
<221> NAME/KEY: MISC_FEATURE
<222> LOCATION: (22)..(22)
<223> OTHER INFORMATION: Where the amino acid located at 22 is an
      uncharged polar amino acid, including Thr, Ser, Tyr, Gly, Gln,
      and Asn
<220> FEATURE:
<221> NAME/KEY: MISC_FEATURE
<222> LOCATION: (26)..(27)
<223> OTHER INFORMATION: Where the amino acids located at 26 and 27 are
      hydrophobic amino acids, including Val, Leu, Ile, Met, Pro, Phe,
      and Ala
<220> FEATURE:
<221> NAME/KEY: MISC_FEATURE
<222> LOCATION: (29)..(30)
<223> OTHER INFORMATION: Where the amino acids located at 29 and 30 are
      hydrophobic amino acids, including Val, Leu, Ile, Met, Pro, Phe,
      and Ala
<220> FEATURE:
<221> NAME/KEY: MISC_FEATURE
<222> LOCATION: (33)..(33)
<223> OTHER INFORMATION: Where the amino acid located at 33 is a
      hydrophobic amino acid, including Val, Leu, Ile, Met, Pro, Phe,
      and Ala
<220> FEATURE:
<221> NAME/KEY: MISC_FEATURE
<222> LOCATION: (35)..(35)
```

-continued

```
<223> OTHER INFORMATION: Where the amino acid located at 35 is an
      uncharged polar amino acid, including Thr, Ser, Tyr, Gly, Gln,
      and Asn
<220> FEATURE:
<221> NAME/KEY: MISC_FEATURE
<222> LOCATION: (37)..(38)
<223> OTHER INFORMATION: Where the amino acids located at 37 and 38
      are hydrophobic amino acids, including Val, Leu, Ile, Met, Pro,
      Phe, and Ala

<400> SEQUENCE: 6

Xaa Xaa Cys Glu Xaa Cys Glu Xaa Xaa Xaa Lys Glu Xaa Xaa Lys Xaa
1               5                   10                  15

Xaa Asp Asn Asn Lys Xaa Glu Lys Glu Xaa Xaa Asp Xaa Xaa Asp Lys
            20                  25                  30

Xaa Cys Xaa Lys Xaa Xaa
        35
```

FUSOGENIC PROPERTIES OF SAPOSIN C AND RELATED PROTEINS AND POLYPEPTIDES FOR APPLICATION TO TRANSMEMBRANE DRUG DELIVERY SYSTEMS

This application is based on and claims priority from U.S. Provisional Patent Application Ser. No. 60/181,754, Xiaoyang Qi filed Feb. 11, 2000.

This work was supported in part by NIH Grant RO1 DK57690-01.

FIELD OF THE INVENTION

The present invention relates to methods of delivering pharmaceutical agents across biological membranes, where the pharmaceutical agent is contained within a phospholipid membrane and delivery is facilitated by a membrane fusion protein. More particularly, the present invention relates to methods for enhancing the transport and delivery of pharmaceutical agents across and/or within dermal and mucosal membranes, where the pharmaceutical agent is contained within a liposome, and delivery is facilitated using saposin C, which is in association with the liposome.

BACKGROUND

Drug Delivery

The therapeutic efficacy of pharmaceutical or therapeutic agents relies on the delivery of adequate doses of a pharmaceutical agent to the site of action. Many modes of delivery have been developed, including, for example, enteral (oral), parenteral (intramuscular, intravenous, subcutaneous), and topical administration. In most instances the administration system is chosen for reliable dosage delivery and convenience.

Typically, parenteral administration is the most reliable means of delivering a pharmaceutical to a patient. See, Goodman et al., Goodman and Gilman's Pharmacological Basis of Therapeutics, Pergamon Press, Ehnsford, N.Y. (1990) and Pratt et al. Principles of Drug Action: The Basis of Pharmacology, Churchill Livingstone, New York, N.Y. (1990). Each parenteral mechanism insures that a prescribed dosage of the pharmaceutical agent is inserted into the fluid compartment of the body where it can be transported. The disadvantage of these modes of delivery is that they require an invasive procedure. The invasive nature of administration is inconvenient, painful and subject to infectious contamination.

Enteral and topical administration are more convenient, generally non-painful, and do not predispose to infection, however both have limited utility. The gastrointestinal and dermal surfaces present formidable barriers to transport and therefore, some pharmaceutical agents are not absorbed across these surfaces. Another drawback to patient directed modes of administration (enteral, topical and subcutaneous) is compliance. Pharmaceutical agents that have a short half-life require multiple daily doses. As the number of doses increases, patient compliance and therapeutic efficacy decrease. Simplified and/or less frequent administration schedules can aid in optimizing patient compliance. Wilson et al. (1991) Harrison's Principles of Internal Medicine, 12th Ed., McGraw-Hill, Inc., New York, N.Y.

The skin is an efficient barrier to the penetration of water soluble substances, and the rate of transdermal pharmaceutical agent absorption is primarily determined by the agent's lipid solubility, water solubility, and polarity. Highly polar or water soluble pharmaceutical agents are effectively blocked by the skin. Even very lipophilic pharmaceutical agents penetrate the dermis very slowly compared with the rate of penetration across cell membranes. See Pratt et al. supra.

Efforts to develop more effective and convenient modes of pharmaceutical administration have led to the development of transdermal delivery systems. Many current transdermal pharmaceutical agent delivery systems rely upon pharmaceutical agents that are absorbed when admixed with inert carriers. See Cooper et al. (1987) "Penetration Enhancers", in Transdermal Delivery of Drugs, Vol. II, Kyodonieus et al., Eds., CRC Press, Boca Raton, Fla. Few pharmaceutical agents fit this profile and those which do are not always predictably absorbed. Various forms of chemical enhancers, such as those enhancing lipophilicity, have been developed to improve transdermal transport when physically mixed with certain therapeutic agents and provide more predictable absorption. See for example, U.S. Pat. Nos. 4,645,502; 4,788,062; 4,816,258; 4,900,555; 3,472,931; 4,006,218; and 5,053,227. Carriers have also been coupled to pharmaceutical agents to enhance intracellular transport. See Ames et al. (1973) Proc. Natl. Acad. Sci. USA, 70:456–458 and (1988) Proc. Int. Symp. Cont. Rel. Bioact. Mater., 15:142.

Fusogenic Proteins and Polypeptides of the Saposin Family

Saposins, a family of small (~80 amino acids) heat stable glycoproteins, are essential for the in vivo hydrolytic activity of several lysosomal enzymes in the catabolic pathway of glycosphingolipids (see Grabowski, G. A., Gatt, S., and Horowitz, M. (1990) *Crit. Rev. Biochem. Mol. Biol.* 25, 385–414; Furst, W., and Sandhoff, K., (1992) *Biochim. Biophys. Acta* 1126, 1–16; Kishimoto, Y., Kiraiwa, M., and O'Brien, J. S. (1992) *J. Lipid. Res.* 33, 1255–1267). Four members of the saposin family, A, B, C, and D, are proteolytically hydrolyzed from a single precursor protein, prosaposin (see Fujibayashi, S., Kao, F. T., Hones, C., Morse, H., Law, M., and Wenger, D. A. (1985) *Am. J. Hum. Genet.* 37, 741–748; O'Brien, J. S., Kretz, K. A., Dewji, N., Wenger, D. A., Esch, F., and Fluharty, A. L. (1988) *Science* 241, 1098–1101; Rorman, E. G., and Grabowski, G. A. (1989) Genomics 5, 486–492; Nakano, T., Sandhoff, K., Stumper, J., Christomanou, H., and Suzuki, K. (1989) *J. Biochem.* (*Tokyo*) 105, 152–154; Reiner, O., Dagan, O., and Horowitz, M. (1989) *J. Mol. Neurosci.* 1, 225–233). The complete amino acid sequences for saposins A, B, C and D have been reported as well as the genomic organization and cDNA sequence of prosaposin (see Fujibayashi, S., Kao, F. T., Jones, C., Morse, H., Law, M., and Wenger, D. A. (1985) Am. J. Hum. Genet. 37, 741–748; O'Brien, J. S., Kretz, K. A., Dewji, N., Wenger, D. A., Esch, F., and Fluharty, A. L. (1988) Science 241, 1098–1101; Rorman, E. G., and Grabowski, G. A. (1989) Genomics 5, 486–492). A complete deficiency of prosaposin with mutation in the initiation codon causes the storage of multiple glycosphingolipid substrates resembling a combined lysosomal hydrolase deficiency (see Schnabel, D., Schroder, M., Furst, W., Klien, A., Hurwitz, R., Zenk, T., Weber, J., Harzer, K., Paton, B. C., Poulos, A., Suzuki, K., and Sandhoff, K. (1992) *J. Biol. Chem.* 267, 3312–3315).

Saposins are defined as sphingolipid activator proteins or coenzymes. Structurally, saposins A, B, C, and D have approximately 50–60% similarity including six strictly conserved cysteine residues (see Furst, W., and Sandhoff, K., (1992) *Biochim. Biophys. Acta* 1126, 1–16) that form three intradomain disulfide bridges whose placements are identical (see Vaccaro, A. M., Salvioli, R., Barca, A., Tatti, M., Ciaffoni, F., Maras, B., Siciliano, R., Zappacosta, F., Amoresano, A., and Pucci, P. (1995) *J. Biol. Chem.* 270, 9953–9960). All saposins contain one glycosylation site with conserved placement in the N-terminal sequence half, but glycosylation is not essential to their activities (see Qi. X., and Grabowski, G. A. (1998) *Biochemistry* 37, 11544–11554; Vaccaro, A. M., Ciaffoni, F., Tatti, M., Salvioli, R., Barca, A., Tognozzi, D., and Scerch, C. (1995) *J. Biol. Chem.* 270, 30576–30580). In addition, saposin A has a second glycosylation site in C-terminal half.

All saposins and saposin-like proteins and domains contain a "saposin fold" when in solution. This fold is a multiple α-helical bundle motif, characterized by a three conserved disulfide structure and several amphipathic polypeptides. Despite this shared saposin-fold structure in solution, saposins and saposin-like proteins have diverse in vivo biological functions in the enhancement of lysosomal sphingolipid (SL) and glycosphingolipid (GSL) degradation by specific hydrolases. Because of these roles, the saposins occupy a central position in the control of lysosomal sphingolipid and glycosphingolipid metabolisms (see Kishimoto, Y., Kiraiwa, M., and O'Brien, J. S. (1992) *J. Lipid. Res.* 33, 1255–1267; Fujibayashi, S., Kao, F. T., Hones, C., Morse, H., Law, M., and Wenger, D. A. (1985) *Am. J. Hum. Genet.* 37, 741–748; O'Brien, J. S., Kretz, K. A., Dewji, N., Wenger, D. A., Esch, F., and Fluharty, A. L. (1988) *Science* 241, 1098–1101).

The structural characteristic of these saposins is of great importance to the diverse mechanisms of activation. Since all of these proteins have high sequence similarity, but different mechanisms of action with lipid membranes, one can speculate that the specific biological functions of saposins and saposin-like proteins are the result of the differential interactions with the biological membrane environments. In vitro, saposin A enhances acid β-glucosidase activity at μM concentration, but saposin C deficiency leads to glucosylceramide storage and a "Gaucher disease-like" phenotype (see Schnable, D., Schroder, M., and Sandhoff, K. (1991) *FEBS Lett.* 284, 57–59; Rafi. M. A., deGala, G., Zhang, X. L., and Wenger, D. A. (1993) *Somat. Cell Mol. Genet.* 19, 1–7). Activation of saposin B takes place through solubilizing and presenting glycosphingolipid substrates to lysosomal enzymes (see Furst, W., and Sandhoff, K., (1992) *Biochim. Biophys. Acta* 1126, 1–16).

Saposin C promotes acid β-glucosidase activity by inducing in the enzyme conformational change at acidic pH (see Berent, S. L., and Radin, N. S. (1981) *Biochim. Biophys. Acta* 664, 572–582; Greenberg, P., Merrill, A. H., Liotta, D. C., and Grabowski, G. A. (1990) *Biochim. Biophys. Acta* 1039, 12–20; Qi. X., and Grabowski, G. A. (1998) *Biochemistry* 37, 11544–11554). This interaction of saposin C with the enzyme occurs on negatively charged phospholipid surfaces. In vitro and ex vivo saposins A and D function to enhance the degradation of galactosylceramide and ceramide/sphingomyelin, respectively (see Harzer, K., Paton, B. C., Christomanou, H., Chatelut, M., Levade, T., Hiraiwa, M. and O'Brien, J. S. (1997) *FEBS Lett.* 417, 270–274; Klien, A., Henseler, M., Klein, C., Suzuki, K., Harzer, K., and Sandhoff, K. (1994) *Biochem. Biophys. Res. Commun,* 200, 1440–1448). Patients lacking the individual saposins B and C showed a variant form of metachromatic leukodystrophy and Gaucher disease, respectively. (see Wenger, D. A., DeGala, G., Williams, C., Taylor, H. A., Stevenson, R. E., Pruitt, J. R., Miller, J., Garen, P. D., and Balentine, J. D. (1989) *Am. J. Med. Genet.* 33, 255–265) (see Christomanou, H., Aignesberger, A., and Linke, R. P. (1986) *Biol. Chem. Hoppe-Seyler* 367, 879–890).

Membrane fusion is a major event in biological systems driving secretion, endocytosis, excocytosis, intracellular transport, fertilization, and muscle development (see Christomanou, H., Chabas, A., Pampols, T., and Guardiola, A. (1989) *Klin, Wochenschr.* 67, 999–1003). Recent experimental evidence generated by this inventor has indicated that saposin-lipid membrane interactions play a critical role in saposin-mediated membrane fusion of lipids thereby facilitating transport of active agents across these biological membranes.

Accordingly, there exists a significant need for nontoxic agents which can improve the delivery or transport of pharmaceutical agents across or through biological membranes. The present invention fulfills these needs.

SUMMARY OF THE INVENTION

As described herein, the present invention comprises a method for delivering a pharmaceutical agent through a biological membrane, wherein the method comprises applying to said membrane a composition comprising anionic phospholipids, a safe and effective amount of the pharmaceutical agent contained within the phospholipids, and a fusogenic protein or polypeptide derived from prosaposin in a pharmaceutically acceptable carrier. The pH of the composition is between about 5.5 and 2, and preferably between about 5.5 and about 3.5. Generally, the concentration of the fusogenic protein or polypeptide is of a sufficient amount to deliver the pharmaceutical agent within and/or through the membrane. The concentration of phospholipids are in at least a 10-fold exess to that of the fusogenic protein or polypeptide. The membrane fusion protein is associated with the phospholipid membrane, through electrostatic and hydrophobic and hydrophobic interactions.

In accordance with the present invention, the targeted biological membranes include, but are not limited to, dermal membrane and mucosal membranes. The preferred membrane fusion proteins include saposin C as well as other proteins, polypeptide analogues or polypeptides derived from either saposin C, SEQ. ID. NO. 1, SEQ. ID. NO. 2, SEQ ID No. 3, SEQ. ID No. 4, SEQ ID No. 5 or SEQ ID No. 6. and mixtures thereof.

The phopholipid membranes may be anionic liposomes containing the pharmaceutical agent. The pharmaceutical agent contained within the liposome may comprise large biomolecules and/or small organic molecules. This technology can be used for both cosmetic and medicinal applications in which the objective is delivery of the active agent within and/or beneath the dermal or mucosal membrane.

Finally, the present invention also comprises a method for treating Gauchers Disease, wherein the method comprises the administration of a composition comprising anionic liposomes, a safe and effective amount of acid beta-glucosidase contained within the liposomes; and saposin C, all contained in a pharmaceutically acceptable carrier, wherein the pH of the composition is about 5.5 or less and the saposin C is associated with the surface of the liposome through an electrostatic and hydrophobic interaction. Generally, the concentration of the liposome is in at least a 10-fold excess to that of saposin C.

DETAILED DESCRIPTION OF THE INVENTION

Contents

Figure 1:
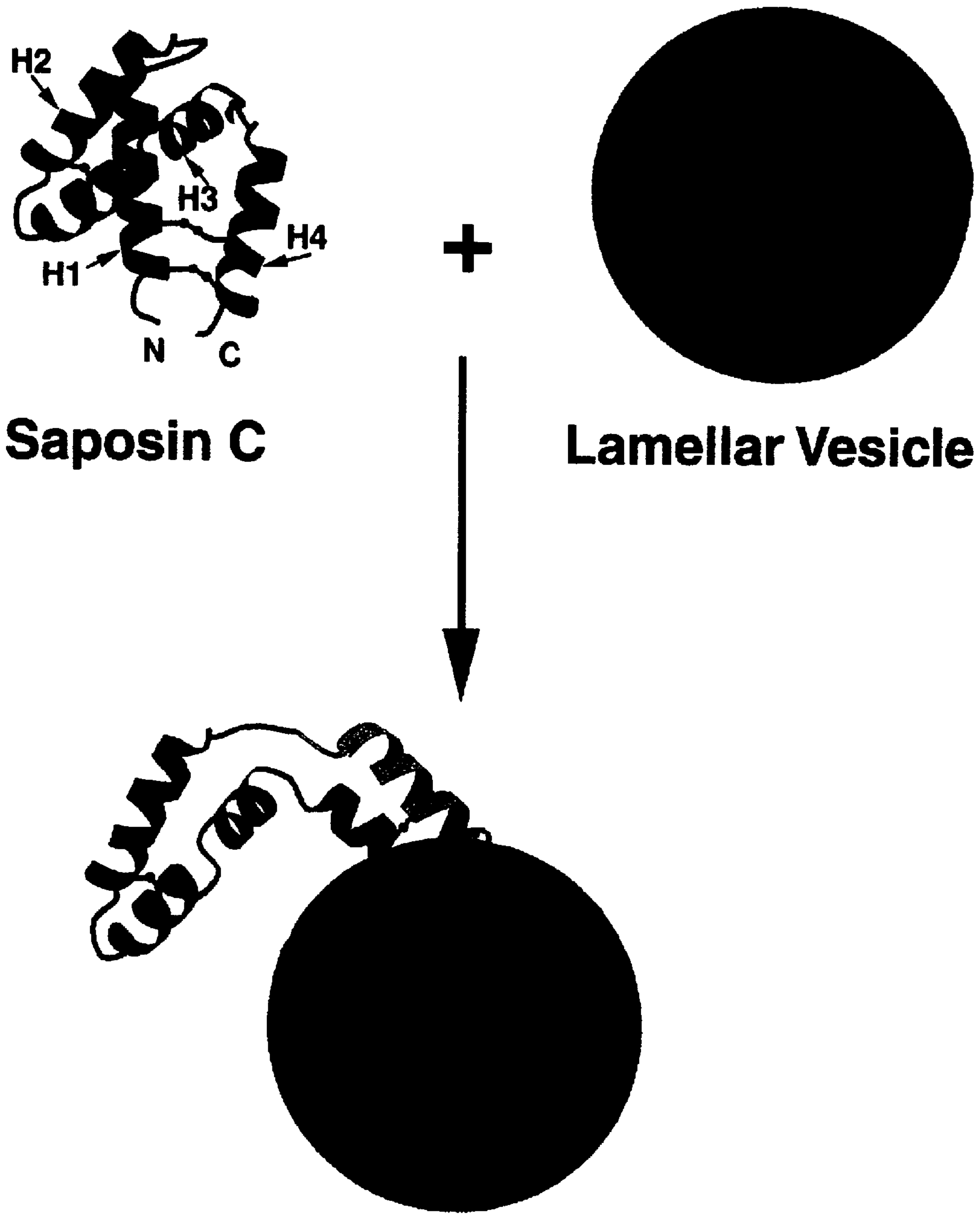
FIG. 1: Clip-on model for saposin C induced fusion: Liposome-bound saposin Cs clip one to another through hydrophobic interaction, and induce liposome fusion.

I. Definitions
II. Fusogenic Proteins or Polypeptides of the Saposin Family
III. The Phospholipid Membrane
IV. Nature and pH Dependence of Protein-Membrane Attachment
V. The Pharmaceutical Agent
  a) General
  b) Digitalis Drugs
  c) Steroidal Compounds
  d) Nonsteroidal Anti-inflammatories
  e) Protein and Peptide Drugs
  f) Nucleotide-based Drugs
  g) Heterocyclic Drugs
VI. Formulation and Delivery of Pharmaceutical Agents
  a) General
  b) Transdermal Delivery
    i. General
    ii. Passive Transdermal Drug Delivery
    iii. Topical Application
  c) Transmucosal Delivery
    i. Buccal Administration
    ii. Nasal Administration
VII. Treatment of Gaucher Disease with Fusogenic Saposin Proteins and Polypeptides
VIII. Experimental Examples I. Definitions The terms "amino acid" or "amino acid sequence," as used herein, refer to an oligopeptide, peptide, polypeptide, or protein sequence, or a fragment of any of these, and to naturally occurring or synthetic molecules. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

The term "amphipathic lipid" means a molecule that has a hydrophilic "head" group and hydrophobic "tail" group and has membrane-forming capability.

As used herein, the terms "anionic phospholipid membrane" and "anionic liposome" refer to a phospholipid membrane or liposome that contains lipid components and has an overall negative charge at physiological pH.

The term "contained (with)in" refers to a pharmaceutical agent being enveloped within a phospholipd membrane, such that the pharmaceutical agent is protected from the outside environment. This term may be used interchangably with "encapsulated."

A "deletion," as the term is used herein, refers to a change in the amino acid or nucleotide sequence that results in the absence of one or more amino acid residues or nucleotides.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological function of the natural molecule. A derivative polypeptide is one modified, for instance by glycosylation, or any other process which retains at least one biological function of the polypeptide from which it was derived.

The term "fusogenic protein or polypeptide" as used herein refers to a protein or peptide that when added to two separate bilayer membranes can bring about their fusion into a single membrane.

The words "insertion" or "addition," as used herein, refer to changes in an amino acid or nucleotide sequence resulting in the addition of one or more amino acid residues or nucleotides, respectively, to the sequence found in the naturally occurring molecule.

The terms "lipid" and "phospholipid" are used interchangeabley and to refer to structures containing lipids, phospholipids, or derivatives thereof comprising a variety of different structural arrangements which lipids are known to adopt in aqueous suspension. These structures include, but are not limited to, lipid bilayer vesicles, micelles, liposomes, emulsions, vesicles, lipid ribbons or sheets. In the preferred embodiment, the lipid is an anioinic liposome. The lipids may be used alone or in any combination which one skilled in the art would appreciate to provide the characteristics desired for a particular application. In addition, the technical aspects of lipid constructs and liposome formation are well known in the art and any of the methods commonly practiced in the field may be used for the present invention.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, or to any DNA-like or RNA-like material. In this context, "fragments" refers to those nucleic acid sequences which, when translated, would produce polypeptides retaining some functional characteristic, e.g., having membrane fusogenic properties, of the full-length polypeptide.

As used herein, the term "nucleotide-based pharmaceutical agent" or "nucleotide-based drug" refer to a pharmaceutical agent or drug comprising a nucleotide, an oligonucleotide or a nucleic acid.

The phrases "percent identity" or "percent homology" refers to the percentage of sequence similarity found in a comparison of two or more amino acid or nucleic acid sequences.

As used herein, "pharmaceutical agent or drug" refers to any chemical or biological material, compound, or composition capable of inducing a desired therapeutic effect when properly administered to a patient. Some drugs are sold in an inactive form that is converted in vivo into a metabolite with pharmaceutical activity. For purposes of the present invention, the terms "pharmaceutical agent" and "drug" encompass both the inactive drug and the active metabolite.

The phrase "pharmaceutically or therapeutically effective dose or amount" refers to a dosage level sufficient to induce a desired biological result. That result may be the delivery of a pharmaceutical agent, alleviation of the signs, symptoms or causes of a disease or any other desired alteration of a biological system and the precise amount of the active depends on the physical condition of the patient, progression of the illness being treated etc.

As used herein, the term "saposin" refers to the family of prosaposin-derived proteins and polypeptides, including but not limited to naturally occurring saposins A, B, C and D as well as synthetic saposin-derived proteins and peptides and peptide analogs showing fusogenic activity. The preferred saposin is saposin C and polypeptides derived therefrom.

As used herein, the terms "transport" and "delivery" refers to the passage of a substance across or through the skin (i.e., transdermal), including the epidermis and dermis, or across a mucosal membrane, where the substance can contact, and be absorbed by the cells of that particular membrane.

II. Fusogenic Proteins or Polypeptides

Suitable lysosomal fusogenic proteins and polypeptides for use in this invention include, but are not limited to, proteins of the saposin family, preferably saposin C. Also included are homologues of saposin C, wherein the homologue possesses at least 80% sequence homology, due to degeneracy of the genetic code which encodes for saposin C, and polypeptides and peptide analogues possessing similar biological activity as saposin C.

Examples of preferred peptide or peptide analogues include:

(SEQ. ID. No. 1)
Ser-Asp-Val-Tyr-Cys-Glu-Val-Cys-Glu-Phe-Leu-Val-Lys-Glu-Val-Thr-Lys-Leu-Ile-Asp-Asn-Asn-Lys-Thr-Glu-Lys-Glu-Ile-Leu-Asp-Ala-Phe-Asp-Lys-Met-Cys-Ser-Lys-Leu-Pro;

(SEQ. ID. No. 2)
Val-Tyr-Cys-Glu-Val-Cys-Glu-Phe-Leu-Val-Lys-Glu-VAl-Thr-Lys-Leu-Ile-Asp-Asn-Asn-Lys-Thr-Glu-Lys-Glu-Ile-Leu-Asp-Ala-Phe-Asp-Lys-Met-Cys-Ser-Lys-Leu-Pro, and derivatives, analogues, homologues, fragments and mixtures thereof.

Also included are polypeptides of the formula:

h-u-Cys-Glu-h-Cys-Glu-h-h-h-Lys-Glu-h-u-Lys-h-h-Asp-Asn-Asn-Lys-u-Glu-Lys-Glu-h-h-Asp-h-h-Asp-Lys-h-Cys-u-Lys-h-h, where h=hydrophobic amino acids, including, Val, Leu, Ile, Met, Pro, Phe, and Ala; and u=uncharged polar amino acids, including, Thr, Ser, Tyr, Gly, Gln, and Asn.

As used herein, term "peptide analog" refers to a peptide which differs in amino acid sequence from the native peptide only by conservative amino acid substitutions, for example, substitution of Leu for Val, or Arg for Lys, etc., or by one or more non-conservative amino acid substitutions, deletions, or insertions located at positions which do not destroy the biological activity of the peptide (in this case, the fusogenic property of the peptide). A peptide analog, as used herein, may also include, as part or all of its sequence, one or more amino acid analogues, molecules which mimic the structure of amino acids, and/or natural amino acids found in molecules other than peptide or peptide analogues.

By "analogs" is meant substitutions or alterations in the amino acid sequences of the peptides of the invention, which substitutions or alterations do not adversely effect the fusogenic properties of the peptides. Thus, an analog might comprise a peptide having a substantially identical amino acid sequence to a peptide provided herein as SEQ ID NO:1 and 2 and in which one or more amino acid residues have been conservatively substituted with chemically similar amino acids. Examples of conservative substitutions include the substitution of a non-polar (hydrophobic) residue such as isoleucine, valine, leucine or methionine for another. Likewise, the present invention contemplates the substitution of one polar (hydrophilic) residue such as between arginine and lysine, between glutamine and asparagine, and between glycine and serine. Additionally, the substitution of a basic residue such as lysine, arginine or histidine for another or the substitution of one acidic residue such as aspartic acid or glutamic acid for another is also contemplated.

III. Phospholipid Membrane

This invention utilizes an anioinic phospholipid membrane to effect the saposin-mediated membrane fusion for delivery of a particular pharmaceutical agent across either a dermal or mucosal membrane. These anionic phospholipid membranes are generally used for preparing liposomes. Liposomes are microscopic vesicles consisting of concentric lipid bilayers and, as used herein, refer to small vesicles composed of amphipathic lipids arranged in spherical bilayers. Structurally, liposomes range in size and shape from long tubes to spheres, with dimensions from a few hundred angstroms to fractions of a millimeter. Regardless of the overall shape, the bilayers are generally organized as closed concentric lamellae, with an aqueous layer separating each lamella from its neighbor. Vesicle size normally falls in a range of between about 20 and about 30,000 nm in diameter. The liquid film between lamellae is usually between about 3 and 10 nm. A variety of methods for preparing various liposome forms have been described in the periodical and patent literature. For specific reviews and information on liposome formulations, reference is made to reviews by Pagano and Weinstein (see Ann. Rev. Biophysic. Bioeng., 7, 435–68 (1978) and Ann. Rev. Biophysic. Bioeng., 9, 467–508 (1980)).

In general, the liposomes utilized in the present invention can be divided into three categories based on their overall size and the nature of the lamellar structure (see New York Academy Sciences Meeting, "Liposomes and Their Use in Biology and Medicine," of December 1977). The four classifications include multi-lamaellar vesicles (MLV's), small uni-lamellar vesicles (SUV's), large unilamellar vesicles (LUV's) and giant unilamellar vesicles (GUV's). SUvs and LUVs, by definition, have only one bilayer, whereas MLVs contain many concentric bilayers.

Liposomes exhibit a wide variety of characteristics, depending upon their size, composition, and charge. For example, liposomes having a small percentage of unsaturated lipids tend to be slightly more permeable, while liposomes incorporating cholesterol or other sterols tend to be more rigid and less permeable. Liposomes may be positive, negative, or neutral in charge, depending on the hydrophilic group. For example, choline-based lipids impart an overall neutral charge, phosphate and sulfate based lipids contribute a negative charge, glycerol-based lipids are generally negatively-charged, and sterols are generally neutral in solution but have charged groups. The lipids used in the present invention are anionic lipids.

In order for many drugs to have therapeutic potential, it is necessary for them to be delivered to the proper location in the body. Liposomes can form the basis for sustained drug release and delivery to specific cell types, or parts of the body. The therapeutic use of liposomes also includes the delivery of drugs which are normally toxic in the free form. In the liposomal form, the toxic drug is occluded, and may be directed away from the tissues sensitive to that drug and targeted to selected areas. Liposomes can also be used therapeutically to release drugs over a prolonged period of time, reducing the frequency of administration. In addition, liposomes can also provide a method for forming aqueous dispersions of hydrophobic or amphiphilic drugs, which are normally unsuitable for intravenous delivery.

The liposomes of the present invention contain pharmaceutical agents, which have been trapped in the aqueous interior or between bilayers, or by trapping hydrophobic molecules within the bilayer. Several techniques can be employed to use liposomes to target encapsulated drugs to selected host tissues, and away from sensitive tissues. These techniques include manipulating the size of the liposomes, their net surface charge, and their route of administration.

The liposomes of the present invention may also be delivered by a passive delivery route. Passive delivery of liposomes involves the use of various routes of administration, e.g., intravenous, subcutaneous, intramuscular and topical. Each route produces differences in localization of the liposomes.

IV. The Nature and pH Dependence of the Protein/Polypeptide-Membrane Association Without intending to be limited by theory, one possible mechanism as to how saposin-mediated membrane fusion occurs is through protein conformational changes. Of the pro-saposin derived proteins, saposin A and saposin C show the highest degree of amino acid identity/similarity. Computationally, both proteins are predicted to fold into amphipathic helical bundle motifs. In general, the saposin-fold is a common super secondary structure with five amphipathic α-helices folded into a single globular domain and is common to both proteins. The presentation of the fold is along a centrally located helix at amino-terminal, against which helices 2 and 3 are packed from one side and helices 4 and 5 from the other side. This fold may provide an interface for membrane interaction.

Figure 2:
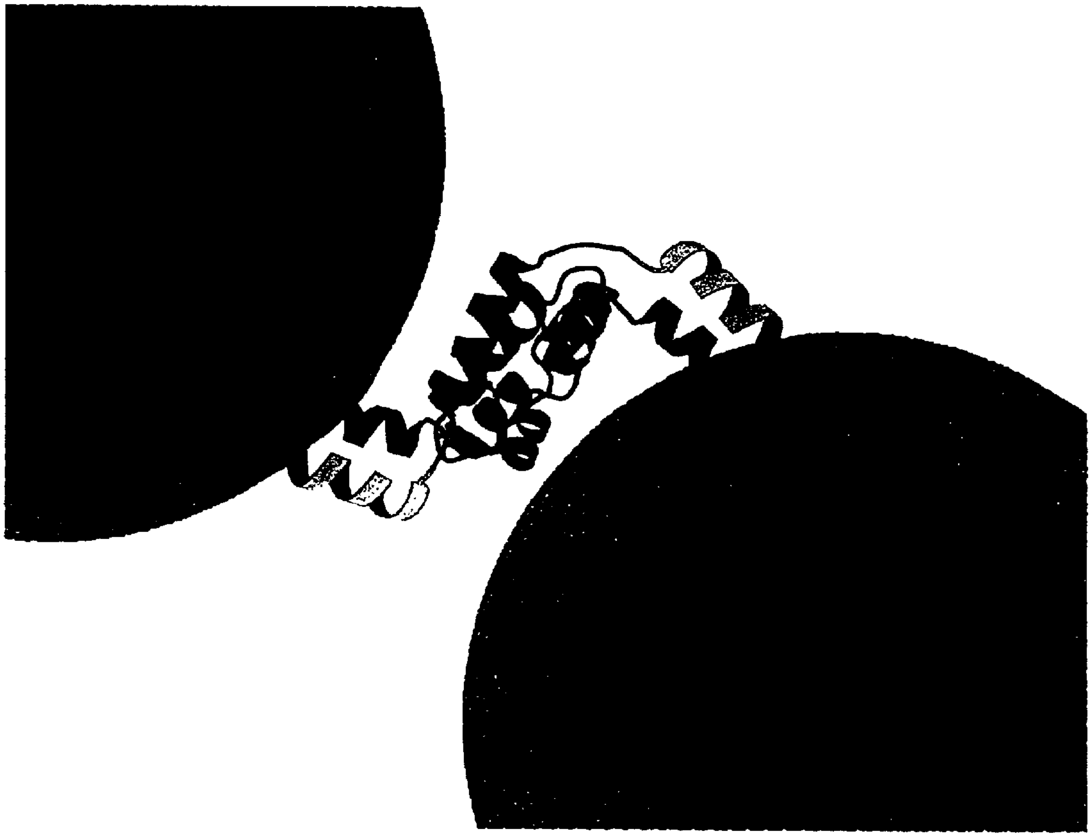
FIG. 2: Saposin C and liposome vesicle association: A conformational alteration of the saposin-fold found in lipid-bound saposin C. Membrane Topological interaction of saposin C indicated that amphipathic helices at amino- and carboxyl-termini were embedded into the lipid bilayer and the middle region of saposin C is exposed to aqueous phase.

A mechanism for saposin-mediated membrane fusion with anionic phospholipid membranes is thought to be a two-step process. In the first step, electrostatic interactions between the positively charged amino acids (Glu and Asp) of the saposins and the negatively charged phospholipid membrane results in an association between these two species (see FIG. 1). In the second step, intramolecular hydrophobic interactions between the helices of two adjacent saposin proteins brings the two membranes in close enough proximity for fusion of the membranes to take place (see FIG. 2).

Thus, in accordance with the present invention, the association of saposins, and in particular saposin C, with a lipid generally requires a pH range from about 5.5 or less since the initial association of saposin C with the membrane arises through an electrostatic interaction of the positively charged basic amino acid residues of saposin C with the anionic membrane. Thus, it is highly desirable to have the basic amino acids exist in their protonated forms in order to achieve a high number of electrostatic interactions.

Alternatively, related fusion proteins and peptides derived from the saposin family of proteins may not have this lower pH range limitation and thus the pH range of other membrane fusion proteins and peptides can range from physiological pH (pH of about 7) to lower pH ranges.

IV. Pharmaceutical Agents

In accordance with the present invention, pharmaceutical agents are contained within the anioinic phospholipid membrane or liposome for saposin-mediated transport within and/or beneath the dermal and mucosal membranes. The active agents may be large biomolecules including, but not limited to lipids, in particular ceramide, steroids, fatty acids, triacylglycerols, genes and proteins. The active agent may also be comprised of small organic molecules. As used herein, "pharmaceutical agent" means any material or mixture of materials which provides a cosmetic or therapeutic benefit when delivered within or through the dermal or mucosal membranes.

a) General

Exemplary pharmaceutical agents or drugs that may be delivered by the system of the present invention may include, but are not limited to, analgesics, anesthetics, antifungals, antibiotics, antiinflammatories, anthelmintics, antidotes, antiemetics, antihistamines, antihypertensives, antimalarials, antimicrobials, antipsychotics, antipyretics, antiseptics, antiarthritics, antituberculotics, antitussives, antivirals, cardioactive drugs, cathartics, chemotherapeutic agents, corticoids (steroids), antidepressants, depressants, diagnostic aids, diuretics, enzymes, expectorants, hormones, hypnotics, minerals, nutritional supplements, parasympathomimetics, potassium supplements, sedatives, sulfonamides, stimulants, sympathomimetics, tranquilizers, urinary antiinfectives, vasoconstrictors, vasodilators, vitamins, xanthine derivatives, and the like.

b) Digitalis Drugs

Preferred examples of pharmaceutical agents include the digitalis drugs, such as digoxin, digitoxin, digoxigenin, and digitoxigenin. These drugs are all primarily used as cardiac agents.

c) Steroidal Compounds

Steroidal compounds form another preferred class of pharmaceutical agent. An example of a steroidal pharmaceutical agent is testosterone (17 beta-hydroxyandrost-4-en-3-one), the principal male steroid. Its main therapeutic use is in the treatment of deficient endocrine function of the testes. Estradiol (estra-1,3,5(10)-triene-3,17 beta-diol) is also a preferred steroidal pharmaceutical agent. Estradiol and its ester derivatives are indicated for the treatment of symptoms of menopause and other conditions that cause a deficiency of endogenous estrogen production. Progesterone is also a preferred steroidal pharmaceutical agent. Progesterone is used primarily to suppress or synchronize estrus as well as to control habitual abortion and diagnose and treat menstrual disorders. Additional preferred steroidal pharmaceutical agents include 3-hydroxy-5 alpha-pregnan-20-one, 3-beta-hydroxy-pregn-5-ene-20-one and related compounds.

d) Nonsteroidal Anti-inflammatory Drugs (NSAID's)

Examples of NSAID's includes piroxicam (4-hydroxy-2-methyl-N-2-pyridinyl-2H-1,2-benzothiazine-3-carboxamide 1,1-dioxide), diclofenac, ibuprofen, ketoprofen, meperidine, propoxyphene, nalbuphine, pentazocine, buprenorphine, asprin, indomethacin, diflunisal, acetominophen, naproxen, fenoprofen, piroxicam, sulindac, tolmetin, meclofenamate, zomepirac, penicillamine, phenylbutazone, oxyphenbutazone, chloroquine, hydroxychloroquine, azathiaprine, cyclophosphamide, levamisole, prednisone, prednisolone, betamethasone, triamcinolone, and methylprednisolone and indomethacin (1-(4-chlorobenzoyl)-5-methoxy-2-methyl-1H-indole-3-acetic acid).

e) Amino Acid-based Drugs

Protein and peptide-based drugs, as well as other amino acid-based drugs, may also be used as pharmaceutical agents according to the present invention. The problems associated with conventional delivery strategies for protein and peptide drugs are widely appreciated. Oral administration of these drugs is generally impractical due to degradation and non-absorption in the gastrointestinal tract. Thus, the parenteral route remains the principal delivery route.

Amino acid-based drugs, such as the cephalosporins, will typically have molecular weight less than about 5000, and preferably, less than about 2500, and more preferably, less than about 1000. Protein and peptide drugs typically have a molecule weight of at least about 100 daltons, and more typically a molecular weight in the range of about 200 to 40,000 daltons. Examples of peptides and proteins in this size range include, but are not limited to Luteinizing hormone-releasing hormone, Somatostatin, Bradykinin, Goserelin, Somatotropin, Buserelin, Platelet-derived growth factor, Triptorelin, Gonadorelin, Asparaginase, Nafarelin, Bleomycin sulfate, Leuprolide, Chymopapain, Growth hormone-releasing factor, parathyroid hormone (PTH), Cholecystokinin, Chorionic gonadotropin, Insulin, Corticotropin (ACTH), Calcitonin Erythropoietin, Glucagon, Hyaluronidase, Interferons, e.g., alpha, Interleukins, e.g., IL-1 Thyrotropin-releasing hormone, Menotropins, Pituitary hormones (e.g. Urofollitropin (Follicle HGH, HMG, HCG, FSH, etc.), Melanocyte-stimulating hormone, Gonadotropin releasing hormone, Oxytocin, Vasopressin, Streptokinase, Tissue plasminogen activator, Angiotensin II antagonists, Bradykinin potentiator B, Bradykinin antagonists, Bradykinin potentiator C, Enkephalins, Insulin-like growth factors, Prostaglandin antagonists, Tumor necrosis factor, Epidermal growth factor (EGF), Amylin, Lipotropin, and Thyroid stimulating hormone.

An example of a preferred peptide pharmaceutical agent is parathyroid hormone (PTH) (see Harper et al., Eds., Review of Physiological Chemistry, 16th Ed., Lange Medical Publications, Los Altos, Calif. (1977) p. 468). Also, a fragment consisting of about 34 amino acid residues from the N-terminal has been isolated and found to display the full biological activity of PTH (see Potts et al., in Parathyroid Hormone and Thyrocalcitonin (Calcitonin), R. V. Talmage, et al., Eds. Excerpta Medica, New York (1968)). The sequence of the polypeptide varies slightly among mammalian species. According to the present invention, PTH is meant to include human parathyroid hormone, as well as the other variants and the 34 amino acid fragment. PTH serves as a regulatory factor in the homeostatic control of calcium and phosphate metabolism (see, e.g., Parsons, et al. "Physiology and Chemistry of Parathyroid Hormone" in Clinics in Endocrinology and Metabolism, I. MacIntyre, Ed. Saunders, Philadelphia (1972) pp. 33–78). The main therapeutic use for PTH is in the treatment of osteoporosis. PTH has also been used as a blood calcium regulator.

Calcitonin is also a preferred peptide pharmaceutical agent. Calcitonin is a polypeptide containing 32 amino acid residues (see Harper et al., Eds., Review of Physiological Chemistry, 16th Ed., Lange Medical Publications, Los Altos, Calif. (1977), p. 469). According to the present invention, calcitonin is meant to include all calcitonin, including that of humans, mammals, and fish, as well as other variants. Calcitonin is a calcium regulating hormone and has been used in the treatment of osteoporosis, hypercalcemia, and Paget's disease.

An additional preferred protein drug is the cytokine IL-10. Il-10 is produced by the TH2 helper subset, B cell subsets and LPs-activated monocytes. IL-10 inhibits several immune functions that are relevant to the skin immune response and thus, the development of the irritation and inflammation that is sometimes associated with the transdermal delivery of drugs. More specifically, the release of IFN-alpha, which initiates the cascade of cellular activation leading to the skin's immune response, is inhibited by IL-10. IL-10 also suppresses the synthesis of numerous pro-inflammatory cytokines by macrophages, as well as the proliferation of antigen-specific T cell proliferation by down regulating class II MHC expression.

e) Nucleic Acid-based Drugs

Generally, nucleic acid-based drugs have had limited success as therapeutic agents, in part, because of problems associated with their stability and delivery. Nucleotide-based pharmaceutical agents frequently contain a phosphodiester bond which is sensitive to degradation by nucleases. Such degradation would be a significant impediment to the use of an oligonucleotide or nucleic acid as a pharmaceutical agent that depends upon the integrity of the sequence for its recognition specificity. Thus, naturally occurring oligonucleotides and nucleic acids often must typically be chemically modified to render them resistant to nucleases which would degrade them in vivo, or even in vitro unless care is taken to choose appropriate conditions. However, this is not necessary using the drug delivery system of the present invention.

The nucleotide-based drugs of the present invention include aptamers, antisense compounds, and triple helix drugs. The nucleotide-based drugs typically will have a molecular weight greater than about 350 and may range up to about 100 bases. Examples of nucleotide-based drugs include di- and trinucleotides, such as GS 375, a dinucleotide analog with potential therapeutic activity against the influenza virus (Gilead Sciences, Inc., Foster City, Calif.).

Aptamers (or nucleic acid antibody) are single- or double-stranded DNA or single-stranded RNA molecules that bind specific molecular targets. Generally, aptamers function by inhibiting the actions of the molecular target, e.g., proteins, by binding to the pool of the target circulating in the blood. Examples of aptamers include Gilead's antithrombin inhibitor GS 522 and its derivatives (Gilead Science, Foster City, Calif.; see also Macaya et al. (1993) Proc. Natl. Acad. Sci. USA 90:3745–9; Bock et al. (1992) Nature (London) 355:564–566; and Wang et al. (1993) Biochem. 32:1899–904).

For diseases that result from the inappropriate expression of genes, specific prevention or reduction of the expression of such genes represents an ideal therapy. In principle, production of a particular gene product may be inhibited, reduced or shut off by hybridization of a single-stranded deoxynucleotide or ribodeoxynucleotide complementary to an accessible sequence in the mRNA, or a sequence within the transcript which is essential for pre-mRNA processing, or to a sequence within the gene itself. This paradigm for genetic control is often referred to as antisense or antigene inhibition.

Antisense compounds are oligonucleotides that are designed to bind and disable or prevent the production of the mRNA responsible for generating a particular protein. Antisense compounds can provide a therapeutic function by inhibiting in vivo the formation of one or more proteins that cause or are involved with disease. Antisense compounds complementary to certain gene messenger RNA or viral sequences have been reported to inhibit the spread of disease related to viral and retroviral infectious agents (see, for example, Matsukura et al. (1987) Proc. Natl. Acad. Sci. USA 84:7706, and references cited therein). Others have reported that oligonucleotides can bind to duplex DNA via triple helix formation and inhibit transcription and/or DNA synthesis.

Antisense compounds include antisense RNA or DNA, single or double stranded, oligonucleotides, or their analogs, which can hybridize specifically to individual MRNA species and prevent transcription and/or RNA processing of the MRNA species and/or translation of the encoded polypeptide and thereby effect a reduction in the amount of the respective encoded polypeptide (see Ching et al. Proc. Natl. Acad. Sci. U.S.A. 86:10006–10010 (1989); Broder et al. Ann. Int. Med. 113:604–618 (1990); Loreau et al. FEBS Letters 274:53–56 (1990)).

Triple helix compounds (also referred to as triple strand drugs) are oligonucleotides that bind to sequences of double-stranded DNA and are intended to inhibit selectively the transcription of disease-causing genes, such as viral genes, e.g., HIV and herpes simplex virus, and oncogenes, i.e., they stop protein production at the cell nucleus. These drugs bind directly to the double stranded DNA in the cell's genome to form a triple helix and thus, prevents the cell from making a target protein (see, for example U.S. Pat. No. 5,176,996, Hogan et al, Jan. 5, 1993).

The site specificity of oligonucleotides (e.g., antisense compounds and triple helix drugs) is not significantly affected by modification of the phosphodiester linkage or by chemical modification of the oligonucleotide terminus. Consequently, these oligonucleotides can be chemically modified; enhancing the overall binding stability, increasing the stability with respect to chemical degradation, increasing the rate at which the oligonucleotides are transported into cells, and conferring chemical reactivity to the molecules. The general approach to constructing various oligonucleotides useful in antisense therapy has been reviewed by vander Krol et al. (1988) Biotechniques 6:958–976 and Stein et al. (1988) Cancer Res. 48:2659–2668.

Accordingly, aptamers, antisense compounds and triple helix drugs also can include nucleotide substitutions, additions, deletions, or transpositions, so long as specific hybridization to or association with the relevant target sequence is retained as a functional property of the oligonucleotide. For example, some embodiments will employ phosphorothioate analogs which are more resistant to degradation by nucleases than their naturally occurring phosphate diester counterparts and are thus expected to have a higher persistence in vivo and greater potency (see, Campbell et al. (1990) J. Biochem. Biophys. Methods 20:259–267). Phosphoramidate derivatives of oligonucleotides also are known to bind to complementary polynucleotides and have the additional capability of accommodating covalently attached ligand species and will be amenable to the methods of the present invention (see Froehler et al. (1988) Nucleic Acids Res. 16(11): 4831).

In addition, nucleotide analogs, for example where the sugar or base is chemically modified, can be employed in the present invention. Analogous forms of purines and pyrimidines are those generally known in the art, many of which are used as chemotherapeutic agents.

Terminal modification also provides a useful procedure to modify cell type specificity, pharmacokinetics, nuclear permeability, and absolute cell uptake rate for oligonucleotide pharmaceutical agents. For example, substitutions at the 5' and 3' ends include reactive groups which allow covalent crosslinking of the nucleotide-based pharmaceutical agent to other species and bulky groups which improve cellular uptake (see Oligodeoxynucleotides: Antisense Inhibitors of Gene Expression, (1989) Cohen, Ed., CRC Press; Prospects for Antisense Nucleic Acid Therapeutics for Cancer and AIDS, (1991), Wickstrom, Ed., Wiley-Liss; Gene Regulation: Biology of Antisense RNA and DNA, (1992) Erickson and Izant, Eds., Raven Press; and Antisense RNA and DNA, (1992), Murray, Ed., Wiley-Liss. For general methods relating to antisense compounds, see Antisense RNA and DNA, (1988), D. A. Melton, Ed., Cold Spring Harbor Laboratory, Cold Spring Harbor, N.Y.).

f) Heterocyclic Drugs

Heterocyclic drugs, and particularly those containing at least one nitrogen heterocyclic ring can be employed as pharmaceutical agents in the methods described herein. For example, yohimbine is an indole alkaloid that blocks alpha-2-adrenergic receptors. Its peripheral effects are to increase cholinergic activity at the same time that it decreases adrenergic activity. This combination has led to the use of yohimbine in the treatment and diagnostic classification of certain types of male erectile impotence.

Other examples of heterocyclic drugs includes, but is not limited to morphine, methotrexate (formerly Amethopterin, N-[4-[[(2,4-diamino-6-pteridinyl)-methyl]methylamino] benzoyl]-L-glutamic acid), Lorazepam (7-chloro-5-(o-chloro-phenyl)-1,3-dihydro-3-hydroxy-2H-1,4-benzodiazepin-2-one), 6-Mercaptopurine, (1,7-dihydro-6H-purine-6-thione monohydrate), 5-fluorouracil, nicotine, nicotinic acid and niacin.

VI. Formulations and Delivery of Pharmaceutical Agents a. General

The compositions of the present invention generally comprise a fusogenic saposin protein or polypeptide, which is associated with an anioinc liposome containing a pharmaceutical agent in a safe and effective amount for the desired effect, all contained in a pharmaceutically acceptable carrier with an appropriate pH. A safe and effective amount of the active agent is defined as an amount which would cause the desired cosmetic or therapeutic effect in a patient. An experienced practioner, skilled in this invention would have knowledge of the appropriate dosing ratios.

The appropriate dosage administered in any given case will, of course, vary depending upon known factors, such as the pharmacodynamic characteristics of the particular pharmaceutical agent, and its mode and route of administration; the age, general health, metabolism, weight of the recipient and other factors which influence response to the compound; the kind of concurrent treatment, the frequency of treatment, and the effect desired.

A preferred embodiment comprises a desired pharmaceutical agent, in a safe and effective amount, which is incorporated into anioinic liposomes, in a buffered aqueous solution of a pH of about 5.5 or less. The preferred fusogenic protein or polypeptide is saposin C, in concentrations from about 20 nM to about 100 nM (nanomolar), preferably about 40 to about 50 nM, which is then introduced to the liposome-pharmacuetical agent mixture. The concentration of the liposomes is in excess to that of the fusogenic protein or polypeptide and is preferably at least in a 10-fold excess, by weight, to that of saposin C (i.e. at least a 1:10 by weight ratio of saposin C:liposome). An electrostatic association occurs between the fusogenic protein or polypeptide and the liposme. Such a composition could then be applied topically to the skin. Other examples of preparing such liposome-fusion protein complexes, in which an active agent is contained within the liposome, are given in U.S. Pat. No. 6,099,857, Gross, Aug. 8, 2000 and U.S. Pat. No. 5,766,626, Gross, Jun. 16, 1998, which are herein incorporated by reference.

b) Transdermal Delivery

The pharmaceutical agent-chemical modifier complexes described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the complex to a patient's skin for an extended period of time. Transdermal patches have the added advantage of providing controlled delivery of a pharmaceutical agent to the body (see Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1–3, Kydonieus and Bemer (eds.), CRC Press, (1987)). Such dosage forms can be made by dissolving, dispersing, or otherwise incorporating the pharmaceutical agent, saposin C and anioinic liposomes in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

i. Passive Transdermal Drug Delivery

A variety of types of transdermal patches will find use in the methods described herein. For example, a simple adhesive patch can be prepared from a backing material and an acrylate adhesive. The pharmaceutical agent-chemical modifier complex and any enhancer are formulated into the adhesive casting solution and allowed to mix thoroughly. The solution is cast directly onto the backing material and the casting solvent is evaporated in an oven, leaving an adhesive film. The release liner can be attached to complete the system.

Alternatively, a polyurethane matrix patch can be employed to deliver the pharmaceutical agent-chemical modifier complex. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast only the backing material.

A further embodiment of this invention will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer.

For passive delivery systems, the rate of release is typically controlled by a membrane placed between the reservoir and the skin, by diffusion from a monolithic device, or by the skin itself serving as a rate-controlling barrier in the delivery system (see U.S. Pat. Nos. 4,816,258; 4,927,408; 4,904,475; 4,588,580, 4,788,062). The rate of drug delivery will be dependent, in part, upon the nature of the membrane. For example, the rate of drug delivery across membranes within the body is generally higher than across dermal barriers. The rate at which the complex is delivered from the device to the membrane is most advantageously controlled by the use of rate-limiting membranes which are placed between the reservoir and the skin. Assuming that the skin is sufficiently permeable to the complex (i.e., absorption through the skin is greater than the rate of passage through the membrane), the membrane will serve to control the dosage rate experienced by the patient.

Suitable permeable membrane materials may be selected based on the desired degree of permeability, the nature of the complex, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Other items may be contained in the device, such as other conventional components of therapeutic products, depending upon the desired device characteristics. For example, the compositions according to this invention may also include one or more preservatives or bacteriostatic agents, e.g., methyl hydroxybenzoate, propyl hydroxybenzoate, chlorocresol, benzalkonium chlorides, and the like. These pharmaceutical compositions also can contain other active ingredients such as antimicrobial agents, particularly antibiotics, anesthetics, analgesics, and antipruritic agents.

ii) Topical Treatments

Another aspect of this invention provides for the topical delivery of pharmaceutical compositions. This treatment regimen is suitable either for the systemic administration of the pharmaceutical agent or for localized therapy, i.e., directly to pathological or diseased tissue.

Typically, the topical formulations will comprise a preparation for delivering the pharmaceutical agent-chemical modifier complex directly to the affected skin comprising the complex, typically in concentrations in the range of from about 0.001% to 10%; preferably, from about 0.01 to about 10%; more preferably, from about 0.1 to about 5%; and most preferably, from about 1 to about 5%, together with a non-toxic, pharmaceutically acceptable topical carrier (see Dermatological Formulations: Percutaneous Absorption, Barry (ed.), Marcel Dekker Inc., (1983); for standard dosages of conventional pharmaceutical agents, see, e.g., Physicians Desk Reference (1992 Edition); and American Medical Association (1992) Drug Evaluations Subscriptions).

Topical preparations can be prepared by combining the pharmaceutical agent-chemical modifier complex with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like. Lotions may be formulated with an aqueous or oily base and will, in general, also include one or more of the following: stabilizing agents, emulsifying agents, dispersing agents, suspending agents, thickening agents, coloring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like.

Dosage forms for the topical administration of a complex of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels also may contain excipients, such as animal and vegetable fats, oils, waxes, paraffins, starch, tragacanth, cellulose derivatives, polyethylene glycols, silicones, bentonites, talc and zinc oxide, or mixtures thereof. Powders and sprays also can contain excipients such as lactose, talc, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

c. Transmucosal Delivery

Although much of the discussion herein has centered on techniques for transdermal delivery, the methods of the present invention are also applicable to the enhanced transport and delivery of pharmaceutical agents through mucosal membranes, such as gastrointestinal, sublingual, buccal, nasal, pulmonary, vaginal, corneal, and ocular membranes (see Mackay et al. (1991) Adv. Drug Del. Rev, 7:313–338). Specifically, there are many similarities between skin and mucosal membranes. For example, the membrane of the buccal cavity is non-keratinized. However, the buccal membrane is similar to the skin because both are stratified with the former consisting of polygonal cells at the basal membrane leading to squamous cells at the surface.

Transmucosal (i.e., sublingual, buccal and vaginal) drug delivery provides for an efficient entry of active substances to systemic circulation and reduce immediate metabolism by the liver and intestinal wall flora. Transmucosal drug dosage forms (e.g., tablet, suppository, ointment, gel, pessary, membrane, and powder) are typically held in contact with the mucosal membrane and disintegrate and/or dissolve rapidly to allow immediate systemic absorption.

i. Buccal Administration

For delivery to the buccal or sublingual membranes, typically an oral formulation, such as a lozenge, tablet, or capsule will be used. The method of manufacture of these formulations are known in the art, including but not limited to, the addition of the pharmaceutical agent-chemical modifier complex to a pre-manufactured tablet; cold compression of an inert filler, a binder, and either a pharmaceutical agent-chemical modifier complex or a substance containing the complex (as described in U.S. Pat. No. 4,806,356 incorporated by reference) and encapsulation.

Another oral formulation is one that can be applied with an adhesive, such as the cellulose derivative, hydroxypropyl cellulose, to the oral mucosa, for example as described in U.S. Pat. No. 4,940,587, incorporated by reference. This buccal adhesive formulation, when applied to the buccal mucosa, allows for controlled release of the pharmaceutical agent-chemical modifier complex into the mouth and through the buccal mucosa.

ii. Nasal/Pulmonary Administration

For delivery to the nasal and/or pulmonary membranes, typically an aerosol formulation will be employed. The term "aerosol" includes any gas-borne suspended phase of the pharmaceutical agent-chemical modifier complex which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of the pharmaceutical agent-chemical modifier complex suspended in air or other carrier gas, which may be delivered by inhalation from an inhaler device.

VII. Treatment of Gaucher Disease with Fusogenic Saposin Proteins and Polypeptides Additionally, saposin C is essential for hydrolysis of glucosylceramides to ceramide in vivo. A deficiency in epidermal glucocerebrosidase results in an altered glucosylceramide to ceramide ratio and this altered ratio is associated with skin barrier abnormalities characterized by Gaucher Disease. It is thought that saposin C is critical to the formation of the epidermal permeability barrier by maintaining physiologic concentrations of glucosylceramide and ceramide in the stratum corneum. According to this model, the role of saposin C in stimulating glucocerebrosidase is mediated by its destabilizing effect on the membranes. Thus, in patients with epidermal glucocerebrosidase deficiency, a topical application of a saposin C-liposome complex, wherein the lipsome contains acid beta glucosidase, the mixture contained in a pharmaceutically acceptable carrier may be used to fuse cell membranes in order to facilitate the hydrolysis of glucosylceramide to ceramide to aid in regulation of skin barrier formation and function. These compositions can, for example, be formulated as creams, lotions, solutions or gels. The carrier may include, for example, pharmaceutically acceptable emollients, emulsifiers, thickening agents, solvents, preservatives, coloring agents and fragrances.

EXPERIMENTAL EXAMPLES

To elucidate the temporal and spatial interaction of saposins with liposomal membranes, the Inventor has focused efforts on the development of intrinsic (Trp) and/or extrinsic (NBD, pyrene, etc.) fluorescence determination methods. These approaches include maximal emission spectrum shift, fluorescence resonance energy transfer, fluorescence stopped-flow analysis, flow-analysis of fluorescent bead-saposin-liposome complexes, and fluorescence microscopy. In addition, circular dichroism (CD) is used to evaluate relative secondary structure changes from lipid-free to lipid-bound saposins. Analyses of the initial results evolved into the proposed hypothesis.

Summarized below are the studies related to the expression, purification, functional analysis, mutagenesis, as well as fluorescence analyses of saposin-phospholipid interaction and membrane fusion.

1. Purification and Characterization of Natural and Recombinant Saposins a. Expression of Saposins from Prokaryotic Systems Although natural saposins have been isolated and characterized, it is important to establish a recombinant expression system to provide an accessible source of large amounts of normal, mutated and Trp-labeled saposins for the proposed investigations. A prokaryotic system was developed, based on the following: 1) Saposins have at least one occupied N-glycosylation site, but, for saposins B and C, occupancy of these sites are not needed for function. 2) Expression of proteins in eukaryotic systems is labor and resource intensive, and slow. In comparison, prokaryotic systems are rapid and give high yields of wild-type and mutant proteins. And 3) The proteins can be labeled with Trp residues as intrinsic fluorescence probes, since wild-type A is the only saposin that contains a natural Trp(37W).

b. Production of Active Saposins in *E. Coli*

Functional saposins were overexpressed in BL21(DE3) cells using a pET 21a series vector. Following IPTG induction at 37° C. or 30° C., large amounts of saposins containing His·Tag were found in the soluble fraction of the disrupted cells. These were conveniently purified to electrophoretic homogeneity on nickel-loaded columns. Alternatively, saposins without His·Tag were generated by introducing a stop codon after protein coding region, and then purified using immuno-affinity columns with T7-taq monoclonal antibody. The purified recombinant saposin C shows excellent activation of acid β-glucosidase and other biologic properties. Circular dichroism spectra, light scattering, and ES-MS analyses were used to evaluate the physical properties of the purified saposins, such as aggregation status and molecular weight. Trp-saposins without His·Tag were also generated for necessary control experiments. The functional integrity of recombinant saposin C was determined using delipidated and homogenous acid β-glucosidase in a liposomal reconstitution system and in neuritogenic assays. Recombinant saposin B function was determined using a sulfatide binding assay. The in vitro function of recombinant saposins B and C are similar to the natural or deglycosylated saposins.

2. Functional Conformations of Saposins Induced by Phospholipids

To determine the specificity of saposin C-phospholipid interaction, a liposomal system was developed using CD, fluorescence emission shifts, and fluorescence quenching methods. Mutated saposins C's, produced to contain individual Trp (W), were termed saposin C(0W), (S37W), and (81W). These Trp-labeled saposin C's were as follows: saposin C(0W) has a Trp preceding the first $NH_2$-terminal amino acid of mature saposin C, saposin C(S37W) has a Trp at residue 37 (i.e., in the middle), and saposin C(81W) has a Trp after the last COOH-terminal amino acid. These substitutions had no effect on the activation properties or CD spectra of saposin C.

a. CD Spectra

Using CD spectroscopy, relative secondary structural changes of recombinant saposins were induced by membrane binding. The relative secondary structural changes of saposins obtained from the acidic, unsaturated phosphatidylserine (PS)/saposin C complexes and the neutral phosphatidylcholine (PC)/saposin B complexes are similar and result in a decrease the β-strand and an increase the α-helix content (Table 1).

TABLE 1

Circular Dichroism (195–250 nm) Analyses of Saposins with Various Phospholipids

| Saposin | % α | % β | % T | % R |
|---|---|---|---|---|
| C Only | 29.9 | 41.7 | 0.0 | 28.4 |
| C + Phosphatidylserine (18:0,0) | 30.1 | 40.4 | 1.4 | 28.1 |
| C + Phosphatidylcholine (18:1,1) | 30.6 | 41.0 | 0.0 | 28.4 |
| C + Phosphatidylserine (18:1,1) | 49.8 | 3.9 | 14.0 | 32.4 |
| B only | 43.7 | 36.6 | 0.0 | 19.7 |
| B + Phosphatidylserine (18:1,1) | 43.8 | 38.8 | 0.0 | 17.9 |
| B + Phosphatidylcholine (18:1,1) | 68.2 | 24.2 | 5.3 | 2.3 |
| A only | 44.0 | 31.9 | 0.0 | 24.1 |
| A + Phosphatidylserine (18:1,1) | 39.3 | 34.9 | 0.5 | 25.4 |

No changes were observed with saposin A and B in the PS (18:1,1) complexes. These results indicate that saposin A and B have a different membrane interaction from that of saposins C. The CD data were collected on a Jasco 710 instrument, and deconvoluted using Yang's method (see Chang, C. T., Wu, C. S., and Yang, J. T. *Anal. Biochem* (1978) 91, 13–31).

b. Fluorescence Emission Spectra

Emission spectra of proteins shift when the tryptophanyl environments change polarity. The fluorescence spectra of saposins A(0W), A(37W), A(81W), C(0W), and C(81W) obtained upon addition of brain phosphatidylserine (BPS) liposomes, showed blue-shifts (Table 2).

TABLE 2

Fluorescence Emission Maxima of Trp-saposins in the Absence and Presence of Brain phosphatidylserine (BPS)

| | Emission Maxima (EM, nm) | | |
|---|---|---|---|
| Saposins | −BPS | +BPS | EM Shifts |
| C(0W) | 339 | 333 | Blue |
| C(S37W) | 351 | 351 | No |
| C(S37W, Q48N) | 345 | 339 | Blue |
| C(S37W, Q48A/E49A) | 338 | 329 | Blue |
| C(81W) | 339 | 323 | Blue |
| A(0W) | 345 | 333 | Blue |
| A(37W) | 351 | 338 | Blue |
| A(37W, G64E) | 344 | 358 | Red |
| A(37W, K63L/G64E/M65V) | 339 | 350 | Red |
| A(81W) | 345 | 336 | Blue |

Experiments conditions: pH 4.7, protein:lipid = 1:20 to 40. No differences were observed at 22 or 37° C..

The blue-shifts suggest interaction of saposins with lipids during complex formation. However, saposin C (S37W) showed no shift in the presence of BPS. This implies that the $NH_2$-(0W) and COOH-(81W) termini of saposin C enter the membrane whereas the middle of the sequence does not. With saposin A, the reverse is true with the middle of the sequence (37W) in the membrane. This means that saposin A-membrane associations are quite different from those of the saposins C. These results are consistent with the CD analysis. Maximal emission wavelength changes were not observed with saposin As or Cs in the presence of neutral EPC nor with PS containing saturated fatty acid chains.

3. Temporal and Spatial Interaction of Saposins and Phospholipid Membranes

To investigate temporal and spatial interactions of saposins and liposomal membrane, fluorescence stopped-flow and quenching approaches were used with Trp as the intrinsic fluorescence probe of the saposins. These experiments allowed identification of regional interactions between saposins and lipid bilayers, and also the kinetics of their binding.

a. Temporal Interactions

Fluorescence intensity increased significantly upon saposin C(0W) binding to synthetic phosphatidylserine [PS (18:1,1)] vesicles at acidic pH. This binding induced change is lipid-concentration dependent and requires at least one unsaturated fatty acid chain. To evaluate the kinetics of this interaction, stopped-flow experiments were conducted the change in fluorescence during saposin C/liposome complex formation was monitored. When saposin C(0W) was mixed with PS(18:1,1) or BPS vesicles, fluorescence of Trp was increased, but the time course of this change was undetectable due to limitation of the machine's capability. Apparently, the interaction of saposin C and unsaturated PS containing membranes occurs within at least 10 ms.

Figure 3:
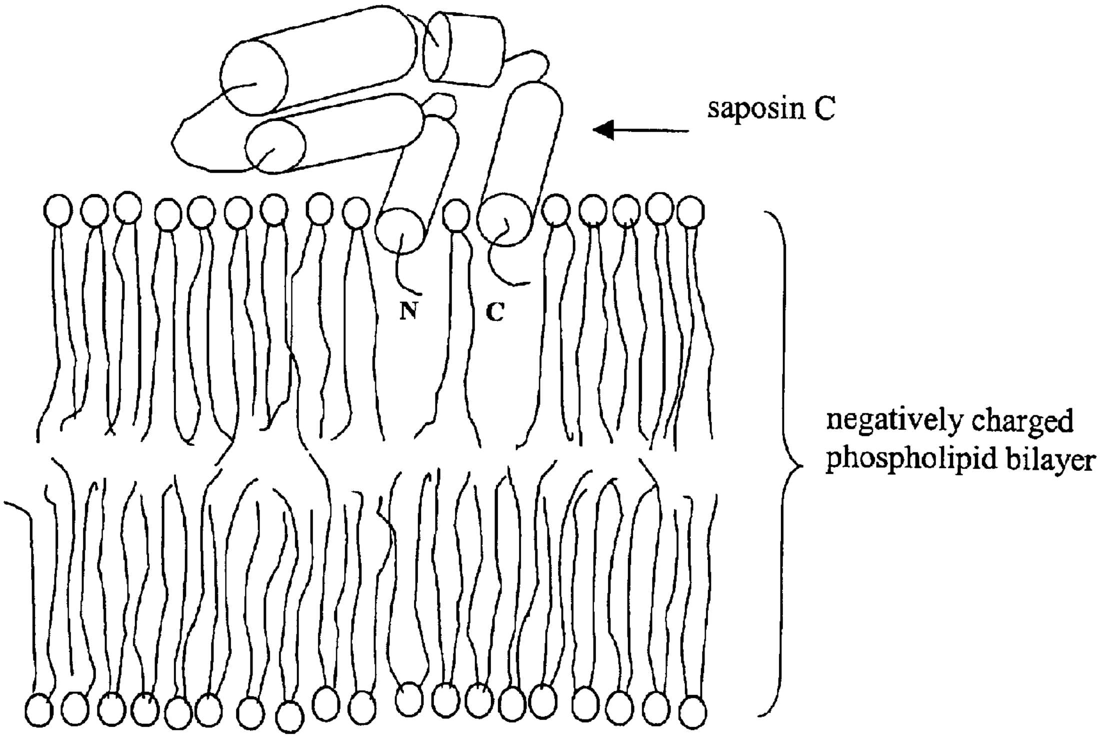
FIG. 3: Hypothetical model of membrane-saposin C interaction. Phospholipid bilayers contain acidic phosphatidylserine. Cylinders are presented in the amphipathic helices in saposin C. The membrane topological structure of saposin C shows a conformational alteration of the saposin fold found in lipid-bound saposin C. The amphipathic helices at amino- and carboxyl termini of saposin C are inserted into the membrane. The middle region of saposin C is exposed to the aqueous phase.

From CD and emission spectra data, saposin C binds negatively charged, unsaturated phospholipids. This suggests there is an electrostatic interaction between positively charged residues in saposin C and the negatively charged membrane surface. This initial interaction is followed by the protein embedding into membrane through a hydrophobic interaction (see FIG. 3). No shift in emission or change in intensity of Trp fluorescence was observed with the saposin C (0W) and PS(18:0,0) mixture.

b. Spatial Interactions

To determine the depth of saposin insertion into BPS liposomes, spin-labeled phosphatidylcholines (SLPCs) were incorporated into BPS liposomes with increasing mole percentages (0–50%). SLPCs, hydrophobic fluorescence quenchers, contain doxyl groups which are located at different carbons (n) in the acyl chain: SLPC5 (n=5), SLPC10 (n=10), and SLPC16 (n=16). After addition of Trp-saposins, the protein-liposome mixture (protein:lipid=1:20) was incubated at room temperature for 30 minutes, and then, the fluorescence intensity changes were recorded. For the Trp-saposins that show the blue-shifts in Table 2, significant quenching effects (30–60%) were observed with BPS/SLPC5 liposomes. The quenching efficiency was dependent upon the location in the acyl chain of the doxyl groups on SLPC. The deeper the doxyl group was in the membrane, the lower quenching efficiency. With BPS/SLPC10, the tryptophanyl fluorescence of saposin C (0W) is quenched by 30%.

4. Saposin C-Induced Membrane Fusion

Figure 4:
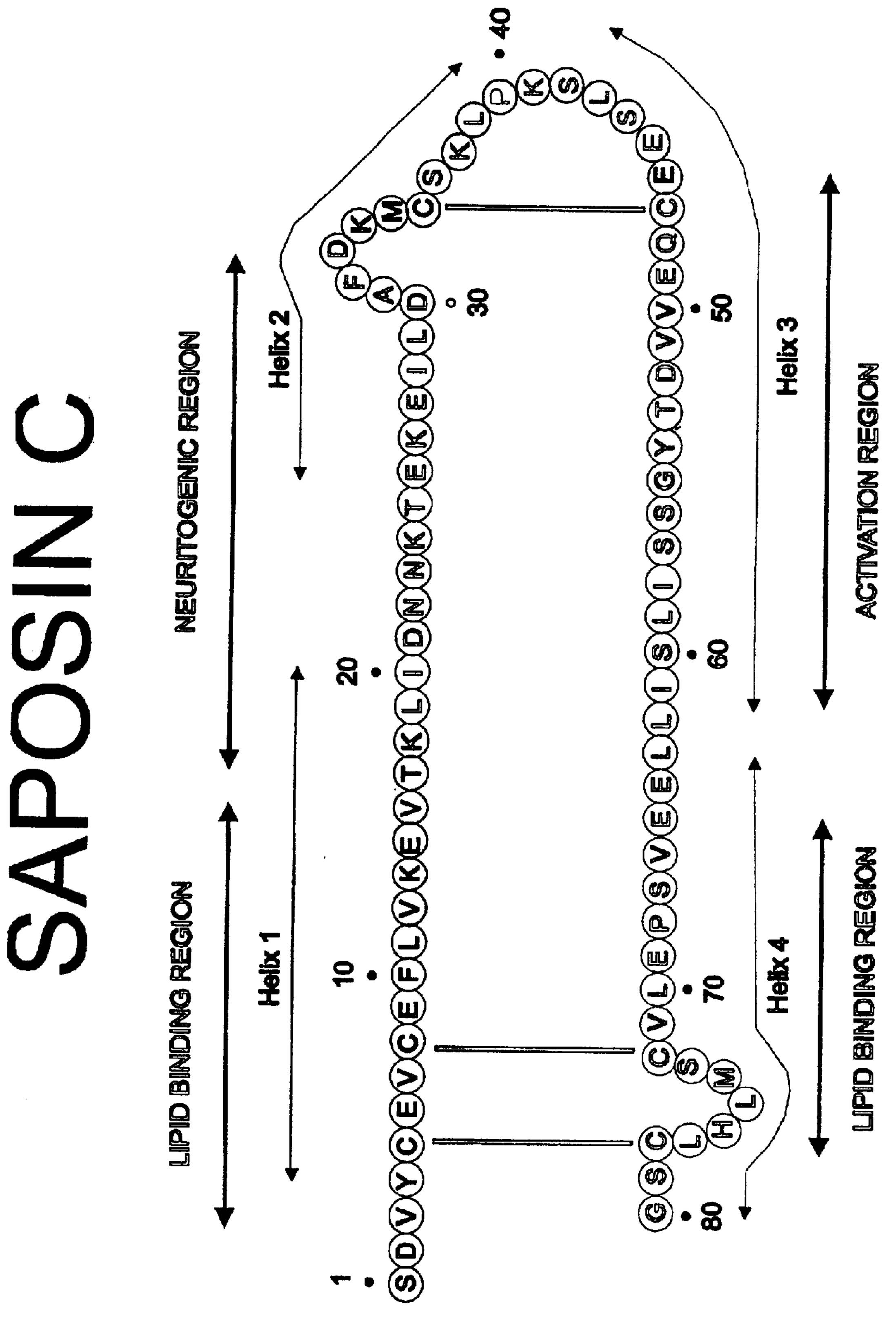
FIG. 4: A schematic of the functional organization of the neuritogenic, acid β-glucosidase activation and lipid-binding properties of saposin C. Except for the box indicating the predicated turn and the disulfide bonds, the figure is not meant to represent known physical structure. The residues from 22–32 are of major significance to the neurotrophic effect. The region spanning residues 42–61 is critical to the acid β-glucosidase activation effects of saposin C, and the presence of all three disulfide bonds is also important for this function. In addition, higher order structure is required to have full activities of saposin C. Lipid/lipid membrane interaction regions are located at both $NH_2$- and COOH-terminal regions.

Saposin C is a multifunctional molecule having lysosomal enzyme activation and neuritogenic activities. Detailed function/structure organization of saposin C is shown in FIG. 4.

The amino acid residues 51–67 are necessary, but not sufficient, for its optimal enzymatic activation function. The disulfide structure and conformational alteration of saposin C upon lipid binding are also required for this activity. Three approaches were used for this study: (1) stopped-flow monitoring reduction of self-quenching resulting from fusion of fluorescence probe-containing vesicle with non-fluorescent vesicle induced by saposin C; (2) monitoring the lipid vesicle size changes upon addition of saposin C to vesicles, the size distribution as determined using N4 plus submicron particle sizer (Coulter Co.); (3) monitoring intrinsic fluorescence of Trp-saposin C change during liposomal fusion. These results defined the fusogenic activity regions at the α-helical domain at amino- and carboxyl-terminus in saposin C, and kinetics of saposin C induced liposomal fusion (see below).

a) Saposin C Induced Liposomal Fusion

Fluorescence probes have been widely used to determine membrane fusion, such as fluorescence dequenching , and fluorescence resonance energy transfer (FET), and can be used for quantitative and kinetics analyses. The dequenching approach was used to investigate saposin C's fusogenic activity. Octadecyl rhodamine B (R18) was selected as fluorescence probe and was entrapped in internal aqueous compartment of liposomal vesicles by co-sonication with BPS or PS(18:1,1). R18 shows self-quenching at high concentrations. Fluorescence increase (dequenching) of R18 occurs upon R18 concentration decreases. After non-labeled and labeled vesicles fuse, the R18 concentration is diluted, resulting in an increase in intensity of fluorescence. R18-labeled vesicles (lipid:R18=96:4, mol:mol) were mixed with the same lipid vesicles without fluorescence probe. Stopped-flow assays were conducted to quickly mix these vesicles with saposin C or $Ca^{2+}$ ion. Time-trace curves were generated for kinetic analysis. Induction of unsaturated PS(18:1,1) membrane fusion by saposin C showed the same kinetics as those with $Ca^{2+}$. Fusion occurs extensively when reaction temperature is above the phase Transition temperature ($T_c$) of phospholipids. The $T_c$ of synthetic PS(18:1) is about −11° C., while the $T_c$ of PS(18:0) is very high (68° C.). Thus, the lipid bilayer phase of PS(18:1,1) is different to that of BPS(18:0 and 18:1) at 24° C. The results indicated that kinetics of saposin C-induced membrane fusion is determined by the physical state of the bilayer lipids.

5. Size Change Determination

Figure 5:
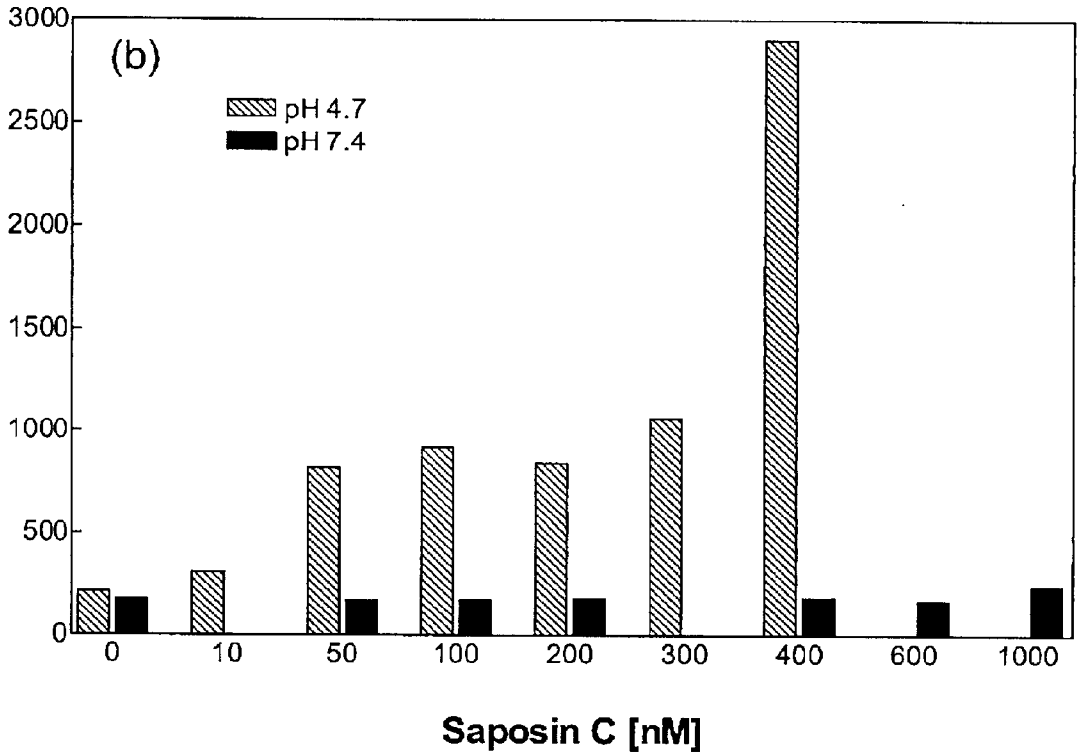
FIG. 5: Size changes of BPS (brain phosphatidylserine) liposomes induced by $Ca^{2+}$ (a) or Saposin C (b) at pH 4.7 or 7.4. Fair autocorrelation function, dust=0.0%, base line error<1%, room temperature.

Electron microscopy (EM) was used for vesicle fusion analysis, since the size of fused vesicles is bigger than those of non-fused. N4 plus submicron particle size was used to estimate particle sizes in the range of 3 nm to 3 μm since most liposomes fit in this range. Sonication conditions with a cup sonicator gave mono-dispersed BPS-liposomes with ~200 nm in size. Upon addition of saposin C, these vesicles changed to a larger size up to 2–3 μm. The size increase is related to vesicles fusion as shown by the above dequenching experiments. Saposin C enlarged vesicle size at pH 4.7, but not at pH 7.4 over a 10 min period (see FIG. 5).

These data suggest a pH-sensitive fusogenic activity of saposin C. Saposin C promotes the size changes at ~50 nM concentration. To define the regions responsible for this fusion property, peptides containing only 50% of the $NH_2$-terminal or 50% of the COOH-terminal halves in saposin C were tested. Both peptides showed fusion activity. These data suggested linear sequence(s) mediated fusion located on both saposin C ends.

6. Mechanism of Fusion

Protein conformational changes are thought to play a role in protein-mediated membrane fusion. This fusion mechanism was evaluated using saposin C-dependent membrane fusion. First, saposin C-PS(18:1,1) liposome complexes were formed. In this saposin C-anchored membrane, protein conformation is altered. This complex is stable from pH 3 to 10, and in low concentrations of SDS solution. This indicated that dissociated rate of saposin C from PS vesicles is very slow.

Since the Trp in saposin C(0W) is embedded inside of lipid bilayer, the change of its signal is indicative of that the surrounding environment of Trp has been changed. After about 20 to 30 ms, Trp fluorescence signal decreased to the starting level. This indicates that saposin C in the complexes interacted with additional PS-vesicles. Shortly after this, the signal dropped back to starting level signaling on end of the fusion process. These data indicate that saposin C retains the fusogenic activity even when it bound to lipid membrane. Therefore, a conformational change of saposin C upon lipid binding is not required for its fusogenic activity. This result is consistent with the conclusion that a linear sequence(s) is sufficient to induce membrane fusion

What is claimed is:

1. A method for delivering a pharmaceutical agent through a membrane, wherein the method comprises applying to said membrane a composition comprising:

a. anionic phospholipid;

b. a safe and effective amount of the pharmaceutical agent contained within the aqueous interior of the phospholipids; and c. a fusogenic protein or polypeptide derived from prosaposm in a pharmaceutically acceptable carrier, wherein the concentration of the fusogenic protein or polypeptide is of a sufficient amount to deliver the pharmaceutical agent through the membrane.

2. The method of claim 1, wherein the concentration of phospholipids are in at least a 10-fold excess, by weight, to that of the fusogenic protein or polypeptide.

3. The method of claim 2 wherein the pH of the composition is between about 5.5 and 2.

4. The method of claim 3 wherein the anionic phospholipid is an anionic liposome.

5. The method of claim 4 wherein the fusogenic protein or polypeptide is associated with the liposome through an electrostatic and hydrophobic interaction.

6. The method of claim 5 wherein the membrane is selected from the group consisting of dermal and mucosal membranes.

7. The method of claim 6 wherein the fusogenic protein or polypeptide is selected from the group consisting of saposin A, saposin C, and mixtures thereof.

8. The method of claim 6 wherein the fusogenic protein or polypeptide is saposin C.

9. The method of claim 6 wherein the fusogenic protein or polypeptide is SEQ ID NO: 1.

10. The method of claim 6 wherein the fusogenic protein or polypeptide is SEQ ID NO: 2.

11. The method of claim 6 wherein the fusogenic protein or polypeptide is selected from the group consisting of those proteins or polypeptides given by SEQ ID NO: 3–6.

12. The method of claim 7 wherein administration of the composition is via a transdermal patch.

13. The method of claim 7 wherein the composition is administered either enterally or topically.

14. A method for delivering a pharmaceutical agent through either a dermal or mucosal membrane, wherein the method comprises the administration to said membrane of a composition comprising:

a. anionic liposomes;

b. a safe and effective amount of the pharmaceutical agent contained within the aqueous interior of the liposomes; and c. saposin C;

in a pharmaceutically acceptable carrier, wherein the concentration of the liposomes are of a sufficient amount to deliver a safe and effective amount of the pharmaceutical agent through the membrane, the pH of the composition is between about 5.5 and 2, and the saposin C is associated with the surface of the liposome through an electrostatic and hydrophobic interaction.

15. The method of claim 14 wherein the concentration of the liposomes is in at least a 10-fold excess, by weight, to that of saposin C.

16. A therapeutic phospholipid composition comprising:

a. an anionic phospholipid;

b. a safe and effective amount of the pharmaceutical agent contained within the agueous interior of the phospholipids; and c. a fusogenic protein or polypeptide derived from prosaposin;

in a pharmaceutically acceptable carrier, wherein the fusogenic protein or polypeptide is present in a sufficient concentration to deliver the pharmaceutical agent through a biological membrane and the fusogenic protein or polypeptide is associated with the phospholipid through an electrostatic and hydrophobic interaction.

17. The therapeutic phospholipid composition of claim 16 wherein the concentration of anionic phospholipid is in at least a 10-fold excess, by weight, to that of the fusogenic protein or polypeptide.

18. The therapeutic phospholipid composition of claim 17 wherein the pH of the composition is between about 5.5 and 2.

19. The therapeutic phospholipid composition of claim 18 wherein the anionic phospholipid is an anionic liposome.

20. The therapeutic phospholipid composition of claim 19 wherein the biological membrane is selected from the group consisting of dermal and mucosal membranes.

21. The therapeutic phospholipid composition of claim 20 wherein the fusogenic protein or polypeptide is selected from the group consisting of saposin A, and saposin C, and mixtures thereof.

22. The therapeutic phospholipid composition of claim 20 wherein the fusogenic protein or polypeptide is saposin C.

23. The therapeutic phospholipid composition of claim 20 wherein the fusogenic protein or polypeptide is SEQ ID NO: 1.

24. The therapeutic phospholipid composition of claim 20 wherein the fusogenic protein or polypeptide is SEQ ID NO: 2.

25. The therapeutic phospholipid composition of claim 20 wherein the fusogenic protein or polypeptide is selected from the group consisting of those proteins or polypeptides given by SEQ ID NO: 3–6.

26. The therapeutic phospholipid composition of claim 21 wherein the composition is formulated as part of a transdermal patch.

27. The therapeutic phospholipid composition of claim 21 wherein the composition is formulated for enteral or topical administration.

28. An anionic liposomal composition used to deliver a pharmaceutical agent through either a dermal or mucosal membrane, wherein the composition comprises:

a. anionic liposomes;

b. a safe and effective amount of the pharmaceutical agent contained within the aqueous interior of the liposomes; and c. saposin C;

in a pharmaceutically acceptable carrier where the pH of the composition is between about 5.5 and 2, wherein the concentration of the saposin C is of a sufficient amount to deliver the pharmaceutical agent through a biological membrane and the saposin C is associated with the surface of the liposomes through an electrostatic and hydrophobic interaction.

29. The anionic liposomal composition of claim 28 wherein the concentration of the anionic liposomes is in at least a 10-fold excess, by weight, to that of saposin C.

30. A composition comprising a safe and effective amount of a pharmaceutical agent contained within the aqueous interior of anionic liposomes, which are associated with a prosaposin-derived fusogenic protein or polypeptide via an electrostatic and hydrophobic interaction, wherein the concentration of the fusogenic protein or polypeptide is of a sufficient amount to deliver the pharmaceutical agent through a biological membrane, the composition contained in a pharmaceutically acceptable carrier, wherein the pH of the composition is between about 5.5 and 2.

31. The composition of claim 30 wherein the concentration of anionic liposomes is in at least a 10-fold excess, by weight, to that of the fusogenic protein or polypeptide.

32. The composition of claim 31 wherein the biological membrane is selected from the group consisting of dermal and mucosal membranes.

33. The composition of claim 32 wherein the fusogenic protein or polypeptide is selected from the group consisting of saposin A, saposin C, and mixtures thereof.

34. The composition of claim 31 wherein the fusogenic protein or polypeptide is saposin C.

35. The composition of claim 31 wherein the fusogenic protein or polypeptide is SEQ ID NO: 1.

36. The composition of claim 31 wherein the fusogenic protein or polypeptide is SEQ ID NO: 2.

37. The composition of claim 31 wherein the fusogenic protein or polypeptide is selected from the group consisting of those proteins or polypeptides given by SEQ ID NO: 3–6.

38. A phospholipid composition used to deliver a pharmaceutical agent through either a dermal or mucosal membrane, wherein the composition comprises:

a. anionic liposomes;

b. a safe and effective amount of the pharmaceutical agent contained within the aqueous interior of the liposomes; and c. saposin C;

in a pharmaceutically acceptable carrier, wherein the pH of the composition is between about 5.5 and 2, the concentration of the saposin C is of a sufficient amount to deliver the pharmaceutical agent through the membrane and the saposin C is associated with the surface of the liposome through an electrostatic and hydrophobic interaction.

39. The phospholipid composition of claim 38 wherein the concentration of the anionic liposomes is in at least a 10-fold excess, by weight, to that of saposin C.

40. The polypeptide consisting of SEQ ID NO: 1.

41. The polypeptide consisting of SEQ ID NO: 2.

42. A compound of the formula consisting of SEQ ID NO: 3–6.

43. A method for treating Gauchers Disease wherein the method comprises the administration of a composition comprising:

a. anionic liposomes;

b. a safe and effective amount of acid beta-glucosidase contained within the aqueous interior of the liposomes; and c. saposin C;

in a pharmaceutically acceptable carrier, wherein the pH of the composition between about 5.5 and 2, the concentration of the saposin C is of a sufficient amount to deliver the pharmaceutical agent through the membrane and the saposin C is associated with the surface of the liposome through an electrostatic and hydrophobic interaction.

44. The method of claim 43 wherein the concentration of the liposome is in at least a 10-fold excess, by weight, to that of saposin C.

* * * * *